United States Patent

Heistracher et al.

[11] Patent Number: 5,807,807
[45] Date of Patent: Sep. 15, 1998

[54] SUBSTITUTED PHTHALIMIDOCINNAMIC ACID DERIVATIVES AND INTERMEDIATES FOR THEIR PREPARATION

[75] Inventors: Elisabeth Heistracher, Ludwigshafen; Peter Plath, Frankenthal; Christoph-Sweder von dem Bussche-Hünnefeld, Mannheim; Gerhard Hamprecht, Weinheim; Ralf Klintz, Gruenstadt; Peter Schäfer, Ottersheim; Karl-Otto Westphalen, Speyer; Helmut Walter, Obrigheim; Matthias Gerber, Limburgerhof; Ulf Misslitz, Neustadt, all of Germany

[73] Assignee: BASF Aktiengesellschaft, Ludwigshafen, Germany

[21] Appl. No.: 928,527

[22] Filed: Sep. 12, 1997

Related U.S. Application Data

[62] Division of Ser. No. 817,326, Apr. 7, 1997, Pat. No. 5,707,937.

[30] Foreign Application Priority Data

Oct. 28, 1994 [DE] Germany .................. 44 38 578.1

[51] Int. Cl.$^6$ .......................... A01N 43/38; C07D 209/48
[52] U.S. Cl. .......................... 504/286; 548/465; 548/476; 560/22; 560/39; 560/41
[58] Field of Search .................. 548/476, 465; 504/286; 560/22, 39, 41

[56] References Cited

U.S. PATENT DOCUMENTS

| | | | |
|---|---|---|---|
| 5,009,701 | 4/1991 | Plath et al. | 504/286 |
| 5,123,955 | 6/1992 | Plath et al. | 504/286 |
| 5,237,089 | 8/1993 | Plath et al. | 560/22 X |
| 5,356,860 | 10/1994 | Schaefer et al. | 504/286 X |

FOREIGN PATENT DOCUMENTS

| | | |
|---|---|---|
| 300387 | 1/1989 | European Pat. Off. . |
| 358108 | 3/1990 | European Pat. Off. . |
| 400427 | 12/1990 | European Pat. Off. . |
| 4237984 | 5/1994 | Germany . |

OTHER PUBLICATIONS

Pirkle et al., Liq Chromat., 16(1), 161–170 (1993).

*Primary Examiner*—Fiona T. Powers
*Attorney, Agent, or Firm*—Keil & Weinkauf

[57] ABSTRACT

Substituted phthalimidocinnamic acid derivatives I

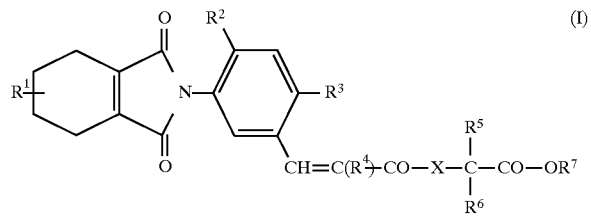

wherein the variables are as defined in the description are useful as herbicides and for the desiccation and/or defoliation of plants.

17 Claims, No Drawings

SUBSTITUTED PHTHALIMIDOCINNAMIC ACID DERIVATIVES AND INTERMEDIATES FOR THEIR PREPARATION

This is a Division of application Ser. No. 08/817,326, filed Apr. 7, 1997, now U.S. Pat. No. 5,707,937.

The present invention relates to novel substituted phthalimidocinnamic acid derivatives of the formula I

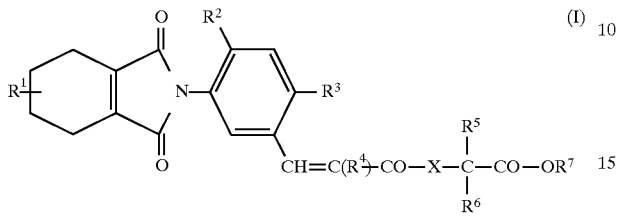

where $R^1$ is hydrogen or $C_1$–$C_4$-alkyl;

$R^2$ is hydrogen or halogen;

$R^3$ is cyano, nitro, halogen, $C_1$–$C_6$-alkyl, $C_1$–$C_6$-haloalkyl, $C_1$–$C_6$-alkoxy or $C_1$–$C_6$-haloalkoxy;

$R^4$ is hydrogen, cyano, nitro, halogen or $C_1$–$C_6$-alkyl;

$R^5$ is hydrogen, $C_1$–$C_6$-alkyl, $C_2$–$C_6$-alkenyl, $C_2$–$C_6$-alkynyl, $C_1$–$C_6$-haloalkyl, $C_1$–$C_6$-cyanoalkyl, $C_1$–$C_6$-hydroxyalkyl, $C_1$–$C_6$-mercaptoalkyl, $C_1$–$C_6$-alkoxy-$C_1$–$C_6$-alkyl or $C_1$–$C_6$-alkylthio-$C_1$–$C_6$-alkyl;

$R^6$ is one of the radicals stated under $R^5$ or cyano, nitro, $C_1$–$C_6$-alkoxy, $C_1$–$C_6$-haloalkoxy, $C_1$–$C_6$-alkylthio, $C_1$–$C_6$-haloalkylthio, $C_3$–$C_6$-cycloalkyl, $C_3$–$C_6$-cycloalkyl-$C_1$–$C_6$-alkyl, ($C_1$–$C_6$-alkoxy)carbonyl-$C_1$–$C_6$-alkyl, hydroxycarbonyl-$C_1$–$C_6$-alkyl, ($C_1$–$C_6$-alkylamino)carbonyl-$C_1$–$C_6$-alkyl, di($C_1$–$C_6$-alkyl)aminocarbonyl-$C_1$–$C_6$-alkyl, aminocarbonyl-$C_1$–$C_6$-alkyl, ($C_1$–$C_6$-alkyl)carbonyl-$C_1$–$C_6$-alkyl, $C_1$–$C_6$-alkoximino-$C_1$–$C_6$-alkyl, hydroximino-$C_1$–$C_6$-alkyl, di($C_1$–$C_6$-alkoxy)-$C_1$–$C_6$-alkyl, di($C_1$–$C_6$-alkylthio)-$C_1$–$C_6$-alkyl, $C_3$–$C_6$-haloalkenyl, ($C_1$–$C_6$-alkoxy)carbonyl, hydroxycarbonyl, ($C_1$–$C_6$-alkylamino)carbonyl, di($C_1$–$C_6$-alkyl)aminocarbonyl, aminocarbonyl($C_1$–$C_6$-alkyl)carbonyl, ($C_1$–$C_6$-haloalkyl) carbonyl, aryl, hetaryl, aryl-$C_1$–$C_6$-alkyl or hetaryl-$C_1$–$C_6$-alkyl, where the aryl and hetaryl rings may, if desired, carry from one to three radicals selected from the group consisting of cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, hydroxyl, mercapto and ($C_1$–$C_6$-alkoxy)carbonyl;

or $R^5$ and $R^6$ together form a two-membered to six-membered alkylene chain in which a methylene unit may be replaced by oxygen or $C_1$–$C_4$-alkylimino;

$R^7$ is hydrogen, $C_1$–$C_6$-alkyl, $C_3$–$C_6$-alkenyl, $C_3$–$C_6$-alkynyl, $C_2$–$C_6$-haloalkyl, $C_1$–$C_6$-cyanoalkyl, $C_1$–$C_6$-alkoxy-$C_2$–$C_6$-alkyl, $C_1$–$C_6$-alkylthio-$C_2$–$C_6$-alkyl, ($C_1$–$C_6$-alkoxy)carbonyl-$C_1$–$C_6$-alkyl, $C_3$–$C_6$-cycloalkyl, $C_3$–$C_6$-cycloalkyl-$C_1$–$C_6$-alkyl, phenyl or benzyl, where the phenyl rings may each carry from one to three radicals selected from the group consisting of cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio and ($C_1$–$C_6$-alkoxy)carbonyl;

X is oxygen, sulfur or —N($R^8$)—, and $R^8$ is one of the radicals stated under $R^7$ or is ($C_1$–$C_6$-alkoxy)carbonyl, ($C_1$–$C_6$-haloalkoxy)carbonyl, ($C_1$–$C_6$-alkyl)carbonyl, ($C_1$–$C_6$-haloalkyl)carbonyl, tri($C_1$–$C_6$-alkyl)silyl, aryloxycarbonyl or arylmethoxycarbonyl or, together with $R^6$, is a three-membered to 5-membered alkylene chain in which a nonterminal methylene unit may be replaced by oxygen or $C_1$–$C_4$-alkylimino or in which the N-bonded methylene unit may be replaced by carbonyl, and the agriculturally useful salts of I.

The present invention furthermore relates to novel intermediates of the formulae IIa and IIb, where $R^2$ to $R^7$ and X have the same meanings as in the case of the compounds I.

The present invention furthermore relates to the use of the compounds I as herbicides and/or for the desiccation and/or defoliation of plants, herbicides and plant desiccants and/or defoliants which contain the compounds I as active ingredients, processes for the preparation of the compounds I and of herbicides and plant desiccants and/or defoliants using the compounds I and methods for controlling undesirable plant growth and for desiccating and/or defoliating plants with the compounds I.

EP-A 240 659, EP-A 300 387 and EP-A 400 427 disclose herbicidal cinnamic acid derivatives. However, their action is not always completely satisfactory, especially at low application rates.

It is an object of the present invention to provide cinnamic acid derivatives having improved herbicidal activity.

We have found that this object is achieved by the substituted phthalimidocinnamic acid derivatives of the formula I which are defined at the outset. We have also found herbicides which contain the compounds I and have very good herbicidal activity. We have furthermore found processes for the preparation of these agents and methods for controlling undesirable plant growth with the compounds I.

The novel compounds I are furthermore suitable for defoliating and desiccating plant parts for, for example, cotton, potato, rape, sunflower, soybeans or field beans, in particular for cotton. Plant desiccants and/or defoliants, processes for the preparation of these agents and methods for desiccating and/or defoliating plants with the compounds I were found for this purpose.

Depending on the substitution pattern, the compounds of the formula I may contain one or more centers of chirality and are then present as enantiomer or diastereomer mixtures. The present invention relates both to the pure enantiomers or diastereomers and to mixtures thereof.

The substituted phthalimidocinnamic acid derivatives I may be present in the form of their agriculturally useful salts, the type of salt generally being unimportant. In general, the salts of those bases and those acid addition salts in which the herbicidal activity is not adversely affected compared with the free compound I are suitable.

Particularly suitable basic salts are those of the alkali metals, preferably sodium and potassium salts, of the alkaline earth metals, preferably calcium and magnesium salts, those of the transition metals, preferably zinc and iron salts, and ammonium salts in which the ammonium ion can, if desired, carry from one to three $C_1$–$C_4$-alkyl or hydroxy-$C_1$–$C_4$-alkyl substituents and/or one phenyl or benzyl substituent, preferably diisopropylammonium, tetramethylammonium, tetrabutylammonium, trimethylbenzylammonium and trimethyl(2-hydroxyethyl)ammonium salts, as well as phosphonium salts, sulfonium salts, preferably tri($C_1$–$C_4$-alkyl)sulfonium salts, and sulfoxonium salts, preferably tri($C_1$–$C_4$-alkyl)sulfoxonium salts.

Among the acid addition salts, the hydrochlorides, hydrobromides, sulfates, nitrates, phosphates, oxalates and dodecylbenzenesulfonates may be mentioned in the first place.

The organic moieties stated for $R^1$ to $R^8$ or as radicals on phenyl, aryl or hetaryl rings are, like the term halogen, general terms for individual lists of the specific group members. All carbon chains, ie. all alkyl, haloalkyl, alkenyl, alkynyl, alkoxy, alkylthio, haloalkoxy, haloalkylthio, alkenyloxy, alkynyloxy, alkoxycarbonyl, alkylimino or alkoximino moieties, may be straight-chain or branched. Halogenated substituents preferably carry from one to five identical or different halogen atoms.

Specific examples are as follows:

halogen is fluorine, chlorine, bromine or iodine;

$C_1$–$C_4$-alkyl is methyl, ethyl, n-propyl, 1-methylethyl, n-butyl, 1-methylpropyl, 2-methylpropyl or 1,1-dimethylethyl;

$C_1$–$C_6$-alkyl and the alkyl moieties of $C_3$–$C_6$-cycloalkyl-$C_1$–$C_6$-alkyl, $C_1$–$C_6$-alkoxy-$C_1$–$C_6$-alkyl, di($C_1$–$C_6$-alkoxy)-$C_1$–$C_6$-alkyl, $C_1$–$C_6$-alkylthio-$C_1$–$C_6$-alkyl, di($C_1$–$C_6$-alkylthio)-$C_1$–$C_6$-alkyl, ($C_1$–$C_6$-alkyl)carbonyl-$C_1$–$C_6$-alkyl, ($C_1$–$C_6$-alkoxy)carbonyl-$C_1$–$C_6$-alkyl, $C_1$–$C_6$-alkoximino-$C_1$–$C_6$-alkyl, ($C_1$–$C_6$-alkylamino)carbonyl-$C_1$–$C_6$-alkyl, di($C_1$–$C_6$-alkyl)aminocarbonyl-$C_1$–$C_6$-alkyl, tri($C_1$–$C_6$-alkyl)silyl, aryl-$C_1$–$C_6$-alkyl and hetaryl-$C_1$–$C_6$-alkyl are each one of the radicals stated for $C_1$–$C_4$-alkyl or are each n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

the alkyl moieties of $C_1$–$C_6$-alkoxy-$C_2$–$C_6$-alkyl and $C_1$–$C_6$-alkylthio-$C_2$–$C_6$-alkyl are each ethyl, n-propyl, 1-methylethyl, n-butyl, 1-methylpropyl, 2-methylpropyl, 1,1-dimethylethyl or one of the radicals additionally stated for $C_1$–$C_6$-alkyl;

$C_2$–$C_6$-haloalkyl is $C_1$–$C_6$-alkyl as stated above, with the exception of methyl which is partially or completely substituted by fluorine, chlorine, bromine and/or iodine, eg. 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_6$-haloalkyl is $C_1$–$C_6$-alkyl as stated above which is partially or completely substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl or one of the radicals stated for $C_2$–$C_6$-haloalkyl;

$C_3$–$C_6$-cycloalkyl and the cycloalkyl moiety of $C_3$–$C_6$-cycloalkyl-$C_1$–$C_6$-alkyl are each cyclopropyl, cyclobutyl, cyclopentyl or cyclohexyl;

$C_3$–$C_6$-alkenyl is prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl or 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl;

$C_2$–$C_6$-alkenyl is ethenyl or one of the radicals stated for $C_3$–$C_6$-alkenyl;

$C_3$–$C_6$-haloalkenyl is $C_3$–$C_6$-alkenyl as stated above which is partially or completely substituted by fluorine, chlorine and/or bromine, eg. 2-chloroallyl, 3-chloroallyl or 3,3-dichloroallyl;

$C_3$–$C_6$-alkynyl is prop-1-yn-1-yl, prop-2-yn-1-yl, but-1-yn-1-yl, but-1-yn-3-yl, but-1-yn-4-yl, but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl;

$C_2$–$C_6$-alkynyl is ethynyl or one of the radicals stated for $C_3$–$C_6$-alkynyl;

$C_1$–$C_6$-cyanoalkyl is cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, 2-cyano-methylprop-2-yl, 1-cyanopent-1-yl, 2-cyanopent-1-yl, 3-cyanopent-1-yl, 4-cyanopent-1-yl, 5-cyanopent-1-yl, 1-cyanopent-2-yl, 2-cyanopent-2-yl, 1-cyanopent-3-yl, 2-cyanopent-3-yl, 1-cyanopent-4-yl, 2-cyanopent-4-yl, 3-cyanopent-4-yl, 1-cyano-2-ethylprop-3-yl, 1-cyanohex-1-yl, 2-cyanohex-1-yl, 3-cyanohex-1-yl, 4-cyanohex-1-yl, 5-cyanohex-1-yl, 6-cyanohex-1-yl, 1-cyanohex-2-yl, 2-cyanohex-2-yl, 1-cyanohex-3-yl, 2-cyanohex-3-yl, 1-cyanohex-4-yl, 2-cyanohex-4-yl, 3-cyanohex-4-yl, 1-cyano-2-ethylbut-3-yl, 1-cyano-2-ethylbut-4-yl or 1-cyano-2-propylprop-3-yl;

$C_1$–$C_6$-hydroxyalkyl is hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxybut-1-yl, 2-hydroxybut-1-yl, 3-hydroxybut-1-yl, 4-hydroxybut-1-yl, 1-hydroxybut-2-yl, 2-hydroxy-but-2-yl, 1-hydroxybut-3-yl, 2-hydroxybut-3-yl, 1-hydroxy-2-methylprop-3-yl, 2-hydroxy-2-methyl-prop-3-yl, 3-hydroxy-2-methylprop-3-yl, 2-hydroxymethylprop-2-yl, 1-hydroxypent-1-yl, 2-hydroxypent-1-yl, 3-hydroxypent-1-yl, 4-hydroxypent-1-yl, 5-hydroxypent-1-yl, 1-hydroxypent-2-yl, 2-hydroxypent-2-yl, 1-hydroxypent-3-yl, 2-hydroxypent-3-yl, 1-hydroxypent-4-yl, 2-hydroxypent-4-yl, 3-hydroxypent-4-yl, 1-hydroxy-2-ethylprop-3-yl, 1-hydroxyhex-1-yl, 2-hydroxyhex-1-yl, 3-hydroxyhex-1-yl, 4-hydroxyhex-1-yl, 5-hydroxyhex-1-yl, 6-hydroxyhex-1-yl, 1-hydroxyhex-2-yl, 2-hydroxyhex-2-yl, 1-hydroxyhex-3-yl, 2-hydroxyhex-3-yl, 1-hydroxyhex-4-yl, 2-hydroxyhex-4-yl, 3-hydroxyhex-4-yl, 1-hydroxy-2-ethylbut-3-yl, 1-hydroxy-2-ethylbut-4-yl or 1-hydroxy-2-propylprop-3-yl;

$C_1$–$C_6$-mercaptoalkyl is mercaptomethyl, 1-mercaptoeth-1-yl, 2-mercaptoeth-1-yl, 1-mercaptoprop-1-yl, 2-mercaptoprop-1-yl, 3-mercaptoprop-1-yl, 1-mercaptoprop-2-yl, 2-mercaptoprop-2-yl, 1-mercaptobut-1-yl, 2-mercaptobut-1-yl, 3-mercaptobut-1-yl, 4-mercaptobut-1-yl, 1-mercaptobut-2-yl, 2-mercapto-but-2-yl, 1-mercaptobut-3-yl, 2-mercaptobut-3-yl, 1-mercapto-2-methylprop-3-yl, 2-mercapto-2-methylprop-3-yl, 3-mercapto-2-methyl-prop-3-yl, 2-mercaptomethylprop-2-yl, 1-mercaptopent-1-yl, 2-mercaptopent-1-yl, 3-mercaptopent-1-yl, 4-mercaptopent-1-yl, 5-mercaptopent-1-yl, 1-mercaptopent-2-yl, 2-mercaptopent-2-yl, 1-mercaptopent-3-yl, 2-mercaptopent-3-yl, 1-mercaptopent-4-yl, 2-mercaptopent-4-yl, 3-mercaptopent-4-yl, 1-mercapto-2-ethyl-prop-3-yl, 1-mercaptohex-1-yl, 2-mercaptohex-1-yl, 3-mercaptohex-1-yl, 4-mercaptohex-1-yl, 5-mercaptohex-1-yl, 6-mercaptohex-1-yl, 1-mercaptohex-2-yl, 2-mercaptohex-2-yl, 1-mercaptohex-3-yl, 2-mercaptohex-3-yl, 1-mercaptohex-4-yl, 2-mercaptohex-4-yl, 3-mercaptohex-4-yl, 1-mercapto-2-ethylbut-3-yl, 1-mercapto-2-ethylbut-4-yl or 1-mercapto-2-propylprop-3-yl;

hydroxycarbonyl-$C_1$–$C_6$-alkyl is hydroxycarbonylmethyl, 1-(hydroxycarbonyl)eth-1-yl, 2-(hydroxycarbonyl)eth-1-yl, 1-(hydroxycarbonyl)prop-1-yl, 2-(hydroxycarbonyl)prop-1-yl, 3-(hydroxycarbonyl)prop-1-yl, 1-(hydroxycarbonyl)prop-2-yl, 2-(hydroxycarbonyl)prop-2-yl, 1-(hydroxycarbonyl)but-1-yl, 2-(hydroxycarbonyl)but-1-yl, 3-(hydroxycarbonyl)but-1-yl, 4-(hydroxycarbonyl)but-1-yl, 1-(hydroxycarbonyl)but-2-yl, 2-(hydroxycarbonyl)but-2-yl, 1-(hydroxycarbonyl)but-3-yl, 2-(hydroxycarbonyl)but-3-yl, 1-(hydroxycarbonyl)-2-methylprop-3-yl, 2-(hydroxycarbonyl)-2-methylprop-3-yl, 3-(hydroxycarbonyl)-2-methylprop-3-yl, 2-(hydroxycarbonylmethyl)prop-2-yl, 1-(hydroxycarbonyl)pent-1-yl, 2-(hydroxycarbonyl)pent-1-yl, 3-(hydroxycarbonyl)pent-1-yl, 4-(hydroxycarbonyl)pent-1-yl, 5-(hydroxycarbonyl)pent-1-yl, 1-(hydroxycarbonyl)pent-2-yl, 2-(hydroxycarbonyl)pent-2-yl, 1-(hydroxycarbonyl)pent-3-yl, 2-(hydroxycarbonyl)pent-3-yl, 1-(hydroxycarbonyl)pent-4-yl, 2-(hydroxycarbonyl)pent-4-yl, 3-(hydroxycarbonyl)pent-4-yl, 1-(hydroxycarbonyl)-2-ethylprop-3-yl, 1-(hydroxycarbonyl)hex-1-yl, 2-(hydroxycarbonyl)hex-1-yl, 3-(hydroxycarbonyl)hex-1-yl, 4-(hydroxycarbonyl)hex-1-yl, 5-(hydroxycarbonyl)hex-1-yl, 6-(hydroxycarbonyl)hex-1-yl, 1-(hydroxycarbonyl)hex-2-yl, 2-(hydroxycarbonyl)hex-2-yl, 1-(hydroxycarbonyl)hex-3-yl, 2-(hydroxycarbonyl)hex-3-yl, 1-(hydroxycarbonyl)hex-4-yl, 2-(hydroxycarbonyl)hex-4-yl, 3-(hydroxycarbonyl)hex-4-yl, 1-(hydroxycarbonyl)-2-ethylbut-3-yl, 1-(hydroxycarbonyl)-2-ethylbut-4-yl or 1-(hydroxycarbonyl)-2-propylprop-3-yl;

hydroximino-$C_1$–$C_6$-alkyl is hydroximinomethyl, 1-(hydroximino)eth-1-yl, 2-(hydroximino)eth-1-yl, 1-(hydroximino)prop-1-yl, 2-(hydroximino)prop-1-yl, 3-(hydroximino)prop-1-yl, 1-(hydroximino)prop-2-yl, 2-(hydroximino)prop-2-yl, 1-(hydroximino)but-1-yl, 2-(hydroximino)but-1-yl, 3-(hydroximino)but-1-yl, 4-(hydroximino)but-1-yl, 1-(hydroximino)but-2-yl, 2-(hydroximino)but-2-yl, 1-(hydroximino)but-3-yl, 2-(hydroximino)but-3-yl, 1-(hydroximino)-2-methylprop-3-yl, 2-(hydroximino)-2-methylprop-3-yl, 3-(hydroximino)-2-methylprop-3-yl, 2-(hydroximinomethyl)-prop-2-yl, 1-(hydroximino)pent-1-yl, 2-(hydroximino)pent-1-yl, 3-(hydroximino)pent-1-yl, 4-(hydroximino)pent-1-yl, 5-(hydroximino)pent-1-yl, 1-(hydroximino)pent-2-yl, 2-(hydroximino)pent-2-yl, 1-(hydroximino)pent-3-yl, 2-(hydroximino)pent-3-yl, 1-(hydroximino)pent-4-yl, 2-(hydroximino)pent-4-yl, 3-(hydroximino)pent-4-yl, 1-(hydroximino)-2-ethylprop-3-yl, 1-(hydroximino)hex-1-yl, 2-(hydroximino)hex-1-yl, 3-(hydroximino)hex-1-yl, 4-(hydroximino)hex-1-yl, 5-(hydroximino)hex-1-yl, 6-(hydroximino)hex-1-yl, 1-(hydroximino)hex-2-yl, 2-(hydroximino)hex-2-yl, 1-(hydroximino)hex-3-yl, 2-(hydroximino)hex-3-yl, 1-(hydroximino)hex-4-yl, 2-(hydroximino)hex-4-yl, 3-(hydroximino)hex-4-yl, 1-(hydroximino)-2-ethylbut-3-yl, 1-(hydroximino)-2-ethylbut-4-yl or 1-(hydroximino)-2-propylprop-3-yl;

aminocarbonyl-$C_1$–$C_6$-alkyl is aminocarbonylmethyl, 1-(aminocarbonyl)eth-1-yl, 2-(aminocarbonyl)eth-1-yl, 1-(aminocarbonyl)prop-1-yl, 2-(aminocarbonyl)prop-1-yl, 3-(aminocarbonyl)prop-1-yl, 1-(aminocarbonyl)prop-2-yl, 2-(aminocarbonyl)prop-2-yl, 1-(aminocarbonyl)but-1-yl, 2-(aminocarbonyl)but-1-yl, 3-(aminocarbonyl)but-1-yl, 4-(aminocarbonyl)but-1-yl, 1-(aminocarbonyl)but-2-yl, 2-(aminocarbonyl)but-2-yl, 1-(aminocarbonyl)but-3-yl, 2-(aminocarbonyl)but-3-yl, 1-(aminocarbonyl)-2-methylprop-3-yl, 2-(aminocarbonyl)-2-methylprop-3-yl, 3-(aminocarbonyl)-2-methylprop-3-yl, 2-(aminocarbonylmethyl)prop-2-yl, 1-(aminocarbonyl)pent-1-yl, 2-(aminocarbonyl)pent-1-yl, 3-(aminocarbonyl)pent-1-yl, 4-(aminocarbonyl)pent-1- yl, 5-(aminocarbonyl)pent-1-yl, 1-(aminocarbonyl) pent-2-yl, 2-(aminocarbonyl)pent-2-yl, 1-(aminocarbonyl)pent-3-yl, 2-(aminocarbonyl)pent-3-yl, 1-(aminocarbonyl)pent-4-yl, 2-(aminocarbonyl) pent-4-yl, 3-(aminocarbonyl)pent-4-yl, 1-(aminocarbonyl)-2-ethylprop-3-yl, 1-(aminocarbonyl)hex-1-yl, 2-(aminocarbonyl)hex-1-yl, 3-(aminocarbonyl)hex-1-yl, 4-(aminocarbonyl)hex-1-yl, 5-(aminocarbonyl)hex-1-yl, 6-(aminocarbonyl) hex-1-yl, 1-(aminocarbonyl)hex-2-yl, 2-(aminocarbonyl)hex-2-yl, 1-(aminocarbonyl)hex-3-yl, 2-(aminocarbonyl)hex-3-yl, 1-(aminocarbonyl)hex-4-yl, 2-(aminocarbonyl)hex-4-yl, 3-(aminocarbonyl) hex-4-yl, 1-(aminocarbonyl)-2-ethylbut-3-yl, 1-(aminocarbonyl)-2-ethylbut-4-yl or 1-(aminocarbonyl)-2-propylprop-3-yl;

$C_1$–$C_6$-alkoxy and alkoxy moieties of $C_1$–$C_6$-alkoxy-$C_1$–$C_6$-alkyl, $C_1$–$C_6$-alkoxy-$C_2$–$C_6$-alkyl and di($C_1$–$C_6$-alkoxy)-$C_1$–$C_6$-alkyl are each methoxy, ethoxy, n-propoxy, 1-methylethoxy, n-butoxy, 1-methylpropoxy, 2-methylpropoxy or 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_6$-haloalkoxy is $C_1$–$C_6$-alkoxy as stated above which is partially or completely substituted by fluorine, chlorine, bromine and/or iodine, eg. difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoropentyloxy, 5-chloropentyloxy, 5-bromopentyloxy, 5-iodopentyloxy, undecafluoropentyloxy, 6-fluorohexyloxy, 6-chlorohexyloxy, 6-bromohexyloxy or dodecafluorohexyloxy;

$C_1$–$C_6$-alkylthio and the alkylthio moieties of $C_1$–$C_6$-alkylthio-$C_1$–$C_6$-alkyl, $C_1$–$C_6$-alkylthio-$C_2$–$C_6$-alkyl and di($C_1$–$C_6$-alkylthio)-$C_1$–$C_6$-alkyl are each methylthio, ethylthio, n-propylthio, 1-methylethylthio, n-butylthio, 1-methylpropylthio, 2-methylpropylthio, 1,1-dimethyl-ethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthic, 2-methylpentylthio, 3-methylpentylthio, 4-methylpentylthic, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_6$-haloalkylthio is $C_1$–$C_6$-alkylthio as stated above which is partially or completely substituted by fluorine, chlorine, bromine and/or iodine, eg. difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2,-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2,-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio, 5-fluoropentylthio, 5-chloropentylthio, 5-bromopentylthio, 5-iodopentylthio, undecafluoropentylthio, 6-fluorohexylthio or 6-chlorohexylthio;

($C_1$–$C_6$-alkoxy)carbonyl and the alkoxycarbonyl moiety of ($C_1$–$C_6$-alkoxy)carbonyl-$C_1$–$C_6$-alkyl are each methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl, 1,1-dimethylethoxycarbonyl, n-pentoxycarbonyl, 1-methylbutoxycarbonyl, 2-methylbutoxycarbonyl, 3-methylbutoxycarbonyl, 1,1-dimethylpropoxycarbonyl, 1,2-dimethylpropoxycarbonyl, 2,2-dimethylpropoxycarbonyl, 1-ethylpropoxycarbonyl, hexyloxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropylcarbonyl;

($C_1$–$C_6$-haloalkoxy)carbonyl is ($C_1$–$C_6$-alkoxy)carbonyl as stated above which is partially or completely substituted by fluorine, chlorine and/or bromine, eg. 2-bromoethoxycarbonyl, 2-chloroethoxycarbonyl, 2-fluoroethoxycarbonyl, 2-trifluoromethyl-2-methylethoxycarbonyl or 2-trichloromethyl-2-methylethoxycarbonyl;

($C_1$–$C_6$-alkyl)carbonyl and the alkylcarbonyl moiety of ($C_1$–$C_6$-alkyl)carbonyl-$C_1$–$C_6$-alkyl are each methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

($C_1$–$C_6$-haloalkyl)carbonyl is ($C_1$–$C_6$-alkyl)carbonyl as stated above which is partially or completely substituted by fluorine, chlorine and/or bromine, eg. chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 1-fluoropropionyl, 2-fluoropropionyl, 2,2-difluoropropionyl, 3,3,3-trifluoropropionyl, 3-chloro-3-fluoropropionyl, 3-chloro-3,3-difluoropropionyl, 3,3-dichloro-3-fluoropropionyl, trichloropropionyl or pentafluoropropionyl;

aminocarbonyl($C_1$–$C_6$-alkyl)carbonyl is aminocarbonylmethylcarbonyl, 1-(aminocarbonyl)eth-1-ylcarbonyl, 2-(aminocarbonyl)-eth-1-ylcarbonyl, 1-(aminocarbonyl)prop-1-ylcarbonyl, 2-(aminocarbonyl)prop-1-ylcarbonyl, 3-(aminocarbonyl)prop-1-ylcarbonyl, 1-(aminocarbonyl)prop-2-ylcarbonyl, 2-(aminocarbonyl)prop-2-ylcarbonyl, 1-(aminocarbonyl)but-1-ylcarbonyl, 2-(aminocarbonyl)but-1-ylcarbonyl, 3-(aminocarbonyl)but-1-ylcarbonyl, 4-(aminocarbonyl)but-1-ylcarbonyl, 1-(aminocarbonyl)but-2-ylcarbonyl, 2-(aminocarbonyl)but-2-ylcarbonyl, 1-(aminocarbonyl)but-3-ylcarbonyl, 2-(aminocarbonyl)but-3-ylcarbonyl, 1-(aminocarbonyl)-2-methylprop-3-ylcarbonyl, 2-(aminocarbonyl)-2-methylprop-3-ylcarbonyl, 3-(aminocarbonyl)-2-methylprop-3-ylcarbonyl, 2-(aminocarbonylmethyl)prop-2-ylcarbonyl, 1-(aminocarbonyl)pent-1-ylcarbonyl, 2-(aminocarbonyl)pent-1-ylcarbonyl, 3-(aminocarbonyl)pent-1-ylcarbonyl, 4-(aminocarbonyl)pent-1-ylcarbonyl, 5-(aminocarbonyl)pent-1-ylcarbonyl, 1-(aminocarbonyl)pent-2-ylcarbonyl, 2-(aminocarbonyl)pent-2-ylcarbonyl, 1-(aminocarbonyl)pent-3-ylcarbonyl, 2-(aminocarbonyl)pent-3-ylcarbonyl, 1-(aminocarbonyl)pent-4-ylcarbonyl, 2-(aminocarbonyl)pent-4-ylcarbonyl, 3-(aminocarbonyl)pent-4-ylcarbonyl, 1-(aminocarbonyl)-2-ethylprop-3-ylcarbonyl, 1-(aminocarbonyl)hex-1-ylcarbonyl, 2-(aminocarbonyl)hex-1-ylcarbonyl, 3-(aminocarbonyl)hex-1-ylcarbonyl, 4-(aminocarbonyl)hex-1-ylcarbonyl, 5-(aminocarbonyl)hex-1-ylcarbonyl, 6-(aminocarbonyl)hex-1-ylcarbonyl, 1-(aminocarbonyl)hex-2-ylcarbonyl, 2-(aminocarbonyl)hex-2-ylcarbonyl, 1-(aminocarbonyl)hex-3-ylcarbonyl, 2-(aminocarbonyl)hex-3-ylcarbonyl, 1-(aminocarbonyl)hex-4-ylcarbonyl, 2-(aminocarbonyl)hex-4-ylcarbonyl, 3-(aminocarbonyl)hex-4-ylcarbonyl, 1-(aminocarbonyl)-2-ethylbut-3-ylcarbonyl, 1-(aminocarbonyl)-2-ethylbut-4-yl or 1-(aminocarbonyl)-2-propylprop-3-ylcarbonyl;

$C_1$–$C_4$-alkylimino is methylimino, ethylimino, n-propylimino, 1-methylethylimino, n-butylimino, 1-methylpropylimino, 2-methylpropylimino or 1,1-dimethylethylimino;

the alkoximino moiety of $C_1$–$C_6$-alkoximino-$C_1$–$C_6$-alkyl is methoximino, ethoximino, 1-propoximino, 2-propoximino, 1-methylethoximino, n-butoximino, sec-butoximino, tertbutoximino, 1-methyl-1-propoximino, 2-methyl-1-propoximino, 1-methyl-2-propoximino, 2-methyl-2-propoximino, n-pentyloximino, 2-pentyloximino, 3-pentyloximino, 4-pentyloximino, 1-methyl-1-butoximino, 2-methyl-1-butoximino, 3-methyl-1-butoximino, 1-methyl-2-butoximino, 2-methyl-2-butoximino, 3-methyl-2-butoximino, 1-methyl-3-butoximino, 2-methyl-3-butoximino, 3-methyl-3-butoximino, 1,1-dimethyl-2-propoximino, 1,2-dimethyl-1-propoximino, 1,2-dimethyl-2-propoximino, 1-ethyl-1-propoximino, 1-ethyl-2-propoximino, n-hexyloximino, 2-hexyloximino, 3-hexyloximino, 4-hexyloximino, 5-hexyloximino, 1-methyl-1-pentyloximino, 2-methyl-1-pentyloximino, 3-methyl-1-pentyloximino, 4-methyl-1-pentyloximino, 1-methyl-2-pentyloximino, 2-methyl-2-pentyloximino, 3-methyl-2-pentyloximino, 4-methyl-2-pentyloximino, 1-methyl-3-pentyloximino, 2-methyl-3-pentyloximino, 3-methyl-3-pentyloximino, 4-methyl-3-pentyloximino, 1-methyl-4-pentyloximino, 2-methyl-4-pentyloximino, 3-methyl-4-pentyloximino, 4-methyl-4-pentoximino, 1,1-dimethyl-2-butoximino, 1,1-dimethyl-3-butoximino, 1,2-dimethyl-1-butoximino, 1,2-dimethyl-2-butoximino, 1,2-dimethyl-3-butoximino, 1,3-dimethyl-1-butoximino, 1,3-dimethyl-2-butoximino, 1,3-dimethyl-3-butoximino, 2,2-dimethyl-3-butoximino, 2,3-dimethyl-1-butoximino, 2,3-dimethyl-2-butoximino, 2,3-dimethyl-3-butoximino, 3,3-dimethyl-1-butoximino, 3,3-dimethyl-2-butoximino, 1-ethyl-1-butoximino, 1-ethyl-2-butenoximino, 1-ethyl-3-butoximino, 2-ethyl-1-butoximino, 2-ethyl-2-butoximino, 2-ethyl-3-butoximino, 1,1,2-trimethyl-2-propoximino, 1-ethyl-1-methyl-2-propoximino, 1-ethyl-2-methyl-1-propoximino or 1-ethyl-2-methyl-2-propoximino;

($C_1$–$C_6$-alkylamino)carbonyl and the alkylaminocarbonyl moiety of ($C_1$–$C_6$-alkylamino)carbonyl-$C_1$–$C_6$-alkyl are each, for example, methylaminocarbonyl, ethylaminocarbonyl, n-propylaminocarbonyl, 1-methylethylaminocarbonyl, n-butylaminocarbonylmethyl, 1-methylpropylaminocarbonyl, 2-methylpropylaminocarbonyl, 1,1-dimethylethylaminocarbonyl, n-pentylaminocarbonyl, 1-methylbutylaminocarbonyl, 2-methylbutylaminocarbonyl, 3-methylbutylaminocarbonyl, 1,1-dimethylpropylaminocarbonyl, 2-dimethylpropylaminocarbonyl, 2-dimethylpropylaminocarbonyl, 1-ethylpropylaminocarbonyl, n-hexylaminocarbonyl, 1-methylpentylaminocarbonyl, 2-methylpentylaminocarbonyl, 3-methylpentylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylcarbonyl or 1-ethyl-2-methylpropylaminocarbonyl;

di($C_1$–$C_6$-alkyl)aminocarbonyl and the dialkylaminocarbonyl moiety of di($C_1$–$C_6$-alkyl)aminocarbonyl-$C_1$–$C_6$-alkyl are each, for example, N,N-dimethylaminocarbonylmethyl, N,N-diethylaminocarbonyl, N,N-diisopropylaminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)-aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1,-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(l-methylpropyl)aminocarbonyl or N-(1,1-dimethylethyl)-N-(2-methylpropyl)aminocarbonyl.

Aryl is to be understood as meaning in particular phenyl or naphthyl.

Hetaryl is preferably to be understood as meaning a 5-membered or 6-membered aromatic heterocyclic structure which, if desired, may carry a fused benzene ring. Particularly preferred heteroaromatic structures are 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 1,2,3,4-tetrazol-5-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

In view of the use of the novel compounds of the formula I as herbicides and/or defoliating/desiccating compounds, the variables preferably have the following meanings, each alone or in combination:

$R^1$ is hydrogen or 4-methyl;
$R^2$ is hydrogen, fluorine or chlorine;
$R^3$ is a substituent from the group 3.01–3.48 (Table 1):

TABLE 1

| No. | $R^3$ | No. | $R^3$ | No. | $R^3$ |
|---|---|---|---|---|---|
| 3.01 | F | 3.19 | $CH_2Br$ | 3.37 | O-sec-$C_4H_9$ |
| 3.02 | Cl | 3.20 | $CHBr_2$ | 3.38 | O-tert-$C_4H_9$ |
| 3.03 | Br | 3.21 | $CH_2CH_2F$ | 3.39 | O—$CHF_2$ |
| 3.04 | I | 3.22 | $CH_2CHF_2$ | 3.40 | O—$CF_3$ |
| 3.05 | $CH_3$ | 3.23 | $CH_2CF_3$ | 3.41 | O—$CH_2CH_2F$ |
| 3.06 | $C_2H_5$ | 3.24 | $CHFCH_3$ | 3.42 | O—$CH_2CHF_2$ |
| 3.07 | n-$C_3H_7$ | 3.25 | $CF_2CH_3$ | 3.43 | O—$CH_2CF_3$ |
| 3.08 | i-$C_3H_7$ | 3.26 | $CF_2CF_3$ | 3.44 | O—$CF_2CF_3$ |
| 3.09 | n-$C_4H_9$ | 3.27 | $CH_2CH_2Cl$ | 3.45 | O—$CH_2CH_2Cl$ |
| 3.10 | i-$C_4H_9$ | 3.28 | $CH(Cl)CH_3$ | 3.46 | O—$CH_2CH_2Br$ |
| 3.11 | sec-$C_4H_9$ | 3.29 | $CH_2CH_2Br$ | 3.47 | CN |
| 3.12 | t-$C_4H_9$ | 3.30 | $C(Br)CH_3$ | 3.48 | $NO_2$ |
| 3.13 | $CH_2F$ | 3.31 | $OCH_3$ | | |
| 3.14 | $CHF_2$ | 3.32 | $OCH_2CH_3$ | | |
| 3.15 | $CF_3$ | 3.33 | O-n-$C_3H_7$ | | |
| 3.16 | $CH_2Cl$ | 3.34 | O-i-$C_3H_7$ | | |
| 3.17 | $CHCl_2$ | 3.35 | O-n-$C_4H_9$ | | |
| 3.18 | $CCl_3$ | 3.38 | O-i-$C_4H_9$ | | |

The radicals 3.01–3.05, 3.15, 3.31, 3.39, 3.40, 3.47 or 3.48 are particularly preferred, in particular 3.01–3.04 and 3.47;

$R^4$ is hydrogen, cyano, nitro, fluorine, chlorine, bromine, iodine, methyl, ethyl, n-propyl or 1-methylethyl, in particular hydrogen, cyano, fluorine, chlorine, bromine or methyl;

$R^5$ is a substituent from the group 5.01–5.51 (Table 2):

TABLE 2

| No. | $R^5$ |
|---|---|
| 5.01 | H |
| 5.02 | $CH_3$ |
| 5.03 | $C_2H_5$ |
| 5.04 | n-$C_3H_7$ |
| 5.05 | i-$C_3H_7$ |
| 5.06 | n-$C_4H_9$ |
| 5.07 | i-$C_4H_9$ |
| 5.08 | sec-$C_4H_9$ |
| 5.09 | tert-$C_4H_9$ |
| 5.10 | $CH=CH_2$ |
| 5.11 | $CH_2$—$CH=CH_2$ |
| 5.12 | $CH_2$—$CH=CH$—$CH_3$ |
| 5.13 | $CH=CH_2$—$CH_3$ |
| 5.14 | $C(CH_3)=CH_2$ |
| 5.15 | $CH=C(CH_3)_2$ |
| 5.16 | $C(CH_3)=CH(CH_3)$ |
| 5.17 | $CH_2$—$CH=C(CH_3)_2$ |
| 5.18 | —$C\equiv CH$ |
| 5.19 | $CH_2$—$C\equiv CH$ |
| 5.20 | $C\equiv C$—$CH_3$ |
| 5.21 | $CH_2$—$C\equiv C$—$CH_3$ |
| 5.22 | $CH_2F$ |
| 5.23 | $CH_2Cl$ |
| 5.24 | $CH_2Br$ |
| 5.25 | $CH_2I$ |
| 5.26 | $CHF_2$ |
| 5.27 | $CHCl_2$ |
| 5.28 | $CHBr_2$ |
| 5.29 | $CF_3$ |
| 5.30 | $CH(F)CH_3$ |

TABLE 2-continued

| No. | $R^5$ |
|---|---|
| 5.31 | $CH(Cl)CH_3$ |
| 5.32 | $CH(Br)CH_3$ |
| 5.33 | $CH(I)CH_3$ |
| 5.34 | $CH_2CN$ |
| 5.35 | $CH(CH_3)CN$ |
| 5.36 | $CH_2CH_2CN$ |
| 5.37 | $CH_2OH$ |
| 5.38 | $CH(CH_3)OH$ |
| 5.39 | $CH_2OCH_3$ |
| 5.40 | $CH_2OC_2H_5$ |
| 5.41 | $CH(CH_3)OCH_3$ |
| 5.42 | $CH(CH_3)OC_2H_5$ |
| 5.43 | $CH_2SH$ |
| 5.44 | $CH(CH_3)SH$ |
| 5.45 | $CH_2CH_2SH$ |
| 5.46 | $CH_2SCH_3$ |
| 5.47 | $CH_2SC_2H_5$ |
| 5.48 | $CH(CH_3)SCH_3$ |
| 5.49 | $CH(CH_3)SC_2H_5$ |
| 5.50 | $CH_2CH_2SCH_3$ |
| 5.51 | $CH_2CH_2SC_2H_5$ |

$R^6$ is a substituent from the group 6.01–6.147 (Table 3):

TABLE 3

| No. | $R^5$ |
|---|---|
| 6.01 | H |
| 6.02 | $CH_3$ |
| 6.03 | $C_2H_5$ |
| 6.04 | $n-C_3H_7$ |
| 6.05 | $i-C_3H_7$ |
| 6.06 | $n-C_4H_9$ |
| 6.07 | $i-C_4H_9$ |
| 6.08 | $sec-C_4H_9$ |
| 6.09 | $tert-C_4H_9$ |
| 6.10 | $CH=CH_2$ |
| 6.11 | $CH_2-CH=CH_2$ |
| 6.12 | $CH_2-CH=CH-CH_3$ |
| 6.13 | $CH=CH_2-CH_3$ |
| 6.14 | $C(CH_3)=CH_2$ |
| 6.15 | $CH=C(CH_3)_2$ |
| 6.16 | $C(CH_3)=CH-CH_3$ |
| 6.17 | $CH_2-CH=C(CH_3)_2$ |
| 6.18 | $C\equiv CH$ |
| 6.19 | $CH_2-C\equiv CH$ |
| 6.20 | $C\equiv C-CH_3$ |
| 6.21 | $CH_2-C\equiv C-CH_3$ |
| 6.22 | $CH_2F$ |
| 6.23 | $CH_2Cl$ |
| 6.24 | $CH_2Br$ |
| 6.25 | $CH_2I$ |
| 6.26 | $CHF_2$ |
| 6.27 | $CHCl_2$ |
| 6.28 | $CHBr_2$ |
| 6.29 | $CF_3$ |
| 6.30 | $CH(F)CH_3$ |
| 6.31 | $CH(Cl)CH_3$ |
| 6.32 | $CH(Br)CH_3$ |
| 6.33 | $CH(I)CH_3$ |
| 6.34 | $CH_2CN$ |
| 6.35 | $CH(CH_3)CN$ |
| 6.36 | $CH_2CH_2CN$ |
| 6.37 | $CH_2OH$ |
| 6.38 | $CH(CH_3)OH$ |
| 6.39 | $CH_2OCH_3$ |
| 6.40 | $CH_2OC_2H_5$ |
| 6.41 | $CH(CH_3)OCH_3$ |
| 6.42 | $CH(CH_3)OC_2H_5$ |
| 6.43 | $CH_2SH$ |
| 6.44 | $CH(CH_3)SH$ |
| 6.45 | $CH_2CH_2SH$ |
| 6.46 | $C_2SCH_3$ |
| 6.47 | $C_2SC_2H_5$ |

TABLE 3-continued

| No. | $R^5$ |
|---|---|
| 6.48 | $CH(CH_3)SCH_3$ |
| 6.49 | $CH(CH_3)SC_2H_5$ |
| 6.50 | $CH_2CH_2SCH_3$ |
| 6.51 | $CH_2CH_2SCH_5$ |
| 6.52 | cyclopropyl |
| 6.53 | cyclobutyl |
| 6.54 | cyclopentyl |
| 6.55 | cyclohexyl |
| 6.56 | $CH_2$-cyclopropyl |
| 6.57 | $CH_2$-cyclobutyl |
| 6.58 | $CH_2$-cyclopentyl |
| 6.59 | $CH_2$-cyclohexyl |
| 6.60 | $CH_2CO_2H$ |
| 6.61 | $CH_2CO_2CH_3$ |
| 6.62 | $CH_2CO_2C_2H_5$ |
| 6.63 | $CH_2CO_2CH(CH_3)_2$ |
| 6.64 | $CH(CH_3)CO_2H$ |
| 6.65 | $CH(CH_3)CO_2CH_3$ |
| 6.66 | $CH(CH_3)CO_2C_2H_5$ |
| 6.67 | $CH(CH_3)CO_2CH(CH_3)_2$ |
| 6.68 | $CH_2CH_2COOH$ |
| 6.69 | $CH_2CH_2COOCH_3$ |
| 6.70 | $CH_2CH_2COOC_2H_5$ |
| 6.71 | $CH_2CH_2COOCH(CH_3)_2$ |
| 6.72 | $CH_2CONH_2$ |
| 6.73 | $CH_2CONHCH_3$ |
| 6.74 | $CH_2CON(CH_3)_2$ |
| 6.75 | $CH_2CONHC_2H_5$ |
| 6.76 | $CH_2CON(C_2H_5)_2$ |
| 6.77 | $CH(CH_3)CONH_2$ |
| 6.78 | $CH(CH_3)CONHCH_3$ |
| 6.79 | $CH(CH_3)CON(CH_3)_2$ |
| 6.80 | $CH(CH_3)CONHC_2H_5$ |
| 6.81 | $CH(CH_3)CON(C_2H_5)_2$ |
| 6.82 | $CH_2CH_2CONH_2$ |
| 6.83 | $CH_2CH_2CONHCH_3$ |
| 6.84 | $CH_2CH_2CON(CH_3)_2$ |
| 6.85 | $CH_2CH_2CONHC_2H_5$ |
| 6.86 | $CH_2CH_2CON(C_2H_5)_2$ |
| 6.87 | $CH_2COCH_3$ |
| 6.88 | $CH_2CH_2COCH_3$ |
| 6.89 | $CH_2CH_2COC_2H_5$ |
| 6.90 | $CH_2C(NOCH_3)H$ |
| 6.91 | $CH_2C(NOC_2H_5)H$ |
| 6.92 | $CH_2C(NOCH_3)CH_3$ |
| 6.93 | $CH_2C(NOC_2H_5)CH_3$ |
| 6.94 | $CH_2CH_2C(NOCH_3)H$ |
| 6.95 | $CH_2CH_2C(NOCH_3)CH_3$ |
| 6.96 | $CH_2CH_2C(NOC_2H_5)H$ |
| 6.97 | $CH_2CH_2C(NOC_2H_5)CH_3$ |
| 6.98 | $CH_2C(NOH)H$ |
| 6.99 | $CH_2C(NOH)CH_3$ |
| 6.100 | $CH_2CH_2C(NOH)H$ |
| 6.101 | $CH_2CH_2C(NOH)CH_3$ |
| 6.102 | $CH_2CH(OCH_3)_2$ |
| 6.103 | $CH_2CH(OC_2H_5)_2$ |
| 6.104 | $CH_2CH(SCH_3)_2$ |
| 6.105 | $CH_2CH(SC_2H_5)_2$ |
| 6.106 | $CH_2-C(Cl)=CH_2$ |
| 6.107 | $CH_2-C(Cl)=CCl_2$ |
| 6.108 | COOH |
| 6.109 | $COOCH_3$ |
| 6.110 | $COOC_2H_5$ |
| 6.111 | $COOCH(CH_3)_2$ |
| 6.112 | $CONH_2$ |
| 6.113 | $CONHCH_3$ |
| 6.114 | $CON(CH_3)_2$ |
| 6.115 | $CONH(C_2H_5)$ |
| 6.116 | $CON(C_2H_5)_2$ |
| 6.117 | $COCH_3$ |
| 6.118 | $COC_2H_5$ |
| 6.119 | $COCH(CH_3)_2$ |
| 6.120 | $COCH_2F$ |
| 6.121 | $COCHF_2$ |
| 6.122 | $COCF_3$ |
| 6.123 | $COCH_2Cl$ |
| 6.124 | $COCH_2Cl$ |

TABLE 3-continued

| No. | $R^5$ |
|---|---|
| 6.125 | $COCCl_3$ |
| 6.126 | $COCH_2Br$ |
| 6.127 | $C_6H_5$ |
| 6.128 | $4\text{-}CH_3\text{---}C_6H_5$ |
| 6.129 | $CH_2C_6H_5$ |
| 6.130 | $CH_2\text{---}C_{10}H_7$ |
| 6.131 | $CH_2\text{-}(4\text{-}Cl\text{---}C_6H_4)$ |
| 6.132 | $CH_2\text{-}(4\text{-}OCH_3\text{---}C_6H_4)$ |
| 6.133 | $CH_2\text{-}(2\text{-imidazolyl})$ |
| 6.134 | $CH_2\text{-}(2\text{-thiazolyl})$ |
| 6.135 | $CH_2\text{-}(4\text{-thiazolyl})$ |
| 6.136 | $CH_2\text{-}(5\text{-thiazolyl})$ |
| 6.137 | $OCH_3$ |
| 6.138 | $OCH_2CH_3$ |
| 6.139 | $OCH(CH_3)_2$ |
| 6.140 | $OCHF_2$ |
| 6.141 | $SCH_3$ |
| 6.142 | $SCH_2CH_3$ |
| 6.143 | $SCH(CH_3)_2$ |
| 6.144 | $SCHF_2$ |
| 6.145 | $SCF_3$ |
| 6.146 | $CN$ |
| 6.147 | $NO_2$ | or $R^5$ and $R^6$ together form a substituent from the group (5+6)0.01 to (5+6)0.10 (Table 4):

TABLE 4

| No. | $R^5 + R^6$ |
|---|---|
| (5 + 6).01 | $\text{---}(CH_2)_2\text{---}$ |
| (5 + 6).02 | $\text{---}(CH_2)_3\text{---}$ |
| (5 + 6).03 | $\text{---}(CH_2)_4\text{---}$ |
| (5 + 6).04 | $\text{---}(CH_2)_5\text{---}$ |
| (5 + 6).06 | $\text{---}(CH_2)_6\text{---}$ |
| (5 + 6).06 | $\text{---}CH_2\text{---}O\text{---}$ |
| (5 + 6).07 | $\text{---}CH_2\text{---}O\text{---}CH_2\text{---}CH_2\text{---}$ |
| (5 + 6).08 | $\text{---}CH_2\text{---}CH_2\text{---}O\text{---}CH_2\text{---}CH_2\text{---}$ |
| (5 + 6).09 | $\text{---}CH_2\text{---}CH_2\text{---}NH\text{---}CH_2\text{---}CH_2\text{---}$ |
| (5 + 6).10 | $\text{---}CH_2\text{---}CH_2\text{---}N(CH_3)\text{---}CH_2\text{---}CH_2\text{---}$ |

$R^7$ is a substituent from the group 7.01–7.60 (Table 5):

TABLE 5

| No. | $R^7$ |
|---|---|
| 7.01 | H |
| 7.02 | $CH_3$ |
| 7.03 | $C_2H_3$ |
| 7.04 | $n\text{-}C_2H_7$ |
| 7.05 | $i\text{-}C_3H_7$ |
| 7.06 | $n\text{-}C_4H_9$ |
| 7.07 | $i\text{-}C_4H_9$ |
| 7.08 | $sec\text{-}C_4H_9$ |
| 7.09 | $tert\text{-}C_4H_9$ |
| 7.10 | $CH_2CH\text{=}CH_2$ |
| 7.11 | $CH_2CH\text{=}CH\text{---}CH_3$ |
| 7.12 | $CH(CH_3)CH\text{=}CH_2$ |
| 7.13 | $CH_2\text{---}C\text{≡}CH$ |
| 7.14 | $CH(CH_3)\text{---}C\text{≡}CH$ |
| 7.15 | $CH_2\text{---}C\text{≡}C\text{---}CH_3$ |
| 7.16 | $CHF_2$ |
| 7.17 | $CH_2CH_2F$ |
| 7.18 | $CH_2CH_2Cl$ |
| 7.19 | $CH_2CF_2H$ |
| 7.20 | $CH_2CF_3$ |
| 7.21 | $CH_2CCl_3$ |
| 7.22 | $CH_2CN$ |
| 7.23 | $CH(CH_3)CN$ |
| 7.24 | $CH_2CH_2OCH_3$ |
| 7.25 | $CH_2CH_2OCH_2CH_3$ |

TABLE 5-continued

| No. | $R^7$ |
|---|---|
| 7.26 | $CH_2CH_2SCH_3$ |
| 7.27 | $CH_2CH_2SCH_2CH_3$ |
| 7.28 | $CH_2CO_2CH_3$ |
| 7.29 | $CH_2CO_2CH_2CH_3$ |
| 7.30 | $CH_2CO_2CH(CH_3)_2$ |
| 7.31 | $CH(CH_3)CO_2CH_3$ |
| 7.32 | $CH(CH_3)CO_2CH_2CH_3$ |
| 7.33 | $CH(CH_2CH_3)CO_2CH_3$ |
| 7.34 | $CH(CH_2CH_3)CO_2CH_2CH_3$ |
| 7.35 | cyclopropyl |
| 7.36 | cyclopentyl |
| 7.37 | cyclohexyl |
| 7.38 | $CH_2$-cyclopropyl |
| 7.39 | $CH_2$-cyclopentyl |
| 7.40 | $CH_2$-cyclohexyl |
| 7.41 | phenyl |
| 7.42 | 2-F-phenyl |
| 7.43 | 3-F-phenyl |
| 7.44 | 4-F-phenyl |
| 7.45 | 2-Cl-phenyl |
| 7.46 | 3-Cl-phenyl |
| 7.47 | 4-Cl-phenyl |
| 7.48 | $2\text{-}CH_3$-phenyl |
| 7.49 | $3\text{-}CH_3$-phenyl |
| 7.50 | $4\text{-}CH_3$-phenyl |
| 7.51 | $2\text{-}CF_3$-phenyl |
| 7.52 | $3\text{-}CF_3$-phenyl |
| 7.53 | $4\text{-}CF_3$-phenyl |
| 7.54 | $2\text{-}CH_3O$-phenyl |
| 7.55 | $3\text{-}CH_3O$-phenyl |
| 7.56 | $4\text{-}CH_3O$-phenyl |
| 7.57 | $2\text{-}CO_2CH_3$-phenyl |
| 7.58 | $3\text{-}CO_2CH_3$-phenyl |
| 7.59 | $4\text{-}CO_2CH_3$-phenyl |
| 7.60 | $CH_2$-phenyl |

X is oxygen or $\text{---}N(R^8)\text{---}$;
$R^8$ is a substituent from the group 8.01–8.40 (Table 6)

TABLE 6

| No. | $R^8$ |
|---|---|
| 8.01 | H |
| 8.02 | $CH_3$ |
| 8.03 | $C_2H_5$ |
| 8.04 | $n\text{-}C_3H_7$ |
| 8.05 | $i\text{-}C_3H_7$ |
| 8.06 | $n\text{-}C_4H_9$ |
| 8.07 | $CH_2CH\text{=}CH_2$ |
| 8.08 | $CH_2CH\text{=}CH(CH_3)$ |
| 8.09 | $CH(CH_3)CH\text{=}CH_2$ |
| 8.10 | $CH_2C\text{≡}CH$ |
| 8.11 | $CH(CH_3)C\text{≡}CH$ |
| 8.12 | $CH_2C\text{≡}C\text{---}CH_3$ |
| 8.13 | $CH_2CH_2F$ |
| 8.14 | $CH_2CH_2Cl$ |
| 8.15 | $CH_2CN$ |
| 8.16 | $CH(CH_3)CN$ |
| 8.17 | $CH_2CH_2OCH_3$ |
| 8.18 | $CH_2CH_2OCH_2CH_3$ |
| 8.19 | $CH_2COOCH_3$ |
| 8.20 | $CH_2COOC_2H_5$ |
| 8.21 | $CH(CH_3)COOCH_3$ |
| 8.22 | $CH(CH_3)COOC_2H_5$ |
| 8.23 | cyclopropyl |
| 8.24 | cyclopentyl |
| 8.25 | cyclohexyl |
| 8.26 | phenyl |
| 8.27 | benzyl |
| 8.28 | $CO\text{---}OCH_3$ |
| 8.29 | $CO\text{---}OC_2H_5$ |
| 8.30 | $CO\text{---}OCF_3$ |
| 8.31 | $CO\text{---}OC(CH_3)_2\text{---}CCl_3$ |
| 8.32 | $CO\text{---}CH_3$ |

TABLE 6-continued

| No. | R⁸ |
|---|---|
| 8.33 | CO—$C_2H_5$ |
| 8.34 | CO-(n-$C_3H_7$) |
| 8.35 | CO—$CF_3$ |
| 8.36 | CO—$CH_2Cl$ |
| 8.37 | CO—$CH_2F$ |
| 8.38 | Si($CH_3$)$_3$ |
| 8.39 | Si($C_2H_5$)$_3$ |
| 8.40 | CO-O-benzyl | or $R^6$ and $R^8$ together form one of the following chains: —$CH_2$—$CH_2$—$CH_2$—, —$CH_2$—$CH_2$—$CH_2$—$CH_2$, —CO—$CH_2$—$CH_2$—, —CO—$CH_2$—$CH_2$—$CH_2$—, —$CH_2$—$CH_2$—O—$CH_2$—, —$CH_2$—$CH_2$—NH—$CH_2$— or —$CH_2$—$CH_2$—N($CH_3$)—$CH_2$—.

In view of the use of the substituted phthalimidocinnamic acid derivatives I as herbicides, the compounds Ia (=I where $R^3$ is chlorine, $R^1$, $R^5$ and $R^6$ are each hydrogen and X is oxygen) stated in Table 7 are very particularly preferred:

TABLE 7

(Ia)

structure: tetrahydroisoquinoline-1,3-dione N-substituted with aryl group bearing $R^2$, Cl, and CH=C($R^4$)—CO—O—$CH_2$—CO—O$R^7$

| No. | $R_2$ | $R_4$ | $R_7$ |
|---|---|---|---|
| Ia.001 | H | H | H |
| Ia.002 | F | H | H |
| Ia.003 | Cl | H | H |
| Ia.004 | H | Cl | H |
| Ia.005 | F | Cl | H |
| Ia.006 | Cl | Cl | H |
| Ia.007 | H | Br | H |
| Ia.008 | F | Br | H |
| Ia.009 | Cl | Br | H |
| Ia.010 | H | $CH_3$ | H |
| Ia.011 | F | $CH_3$ | H |
| Ia.012 | Cl | $CH_3$ | H |
| Ia.013 | H | CN | H |
| Ia.014 | F | CN | H |
| Ia.015 | Cl | CN | H |
| Ia.016 | H | H | $CH_3$ |
| Ia.017 | F | H | $CH_3$ |
| Ia.018 | Cl | H | $CH_3$ |
| Ia.019 | H | Cl | $CH_3$ |
| Ia.020 | F | Cl | $CH_3$ |
| Ia.021 | Cl | Cl | $CH_3$ |
| Ia.022 | H | Br | $CH_3$ |
| Ia.023 | F | Br | $CH_3$ |
| Ia.024 | Cl | Br | $CH_3$ |
| Ia.025 | H | $CH_3$ | $CH_3$ |
| Ia.026 | F | $CH_3$ | $CH_3$ |
| Ia.027 | Cl | $CH_3$ | $CH_3$ |
| Ia.028 | H | CN | $CH_3$ |
| Ia.029 | F | CN | $CH_3$ |
| Ia.030 | Cl | CN | $CH_3$ |
| Ia.031 | H | H | $C_2H_5$ |
| Ia.032 | F | H | $C_2H_5$ |
| Ia.033 | Cl | H | $C_2H_5$ |
| Ia.034 | H | Cl | $C_2H_5$ |
| Ia.035 | F | Cl | $C_2H_5$ |
| Ia.036 | Cl | Cl | $C_2H_5$ |
| Ia.037 | H | Br | $C_2H_5$ |
| Ia.038 | F | Br | $C_2H_5$ |
| Ia.039 | Cl | Br | $C_2H_5$ |
| Ia.040 | H | $CH_3$ | $C_2H_5$ |
| Ia.041 | F | $CH_3$ | $C_2H_5$ |
| Ia.042 | Cl | $CH_3$ | $C_2H_5$ |
| Ia.043 | H | CN | $C_2H_5$ |
| Ia.044 | F | CN | $C_2H_5$ |
| Ia.045 | Cl | CN | $C_2H_5$ |
| Ia.046 | H | H | $CH_2CH_2CH_3$ |
| Ia.047 | F | H | $CH_2CH_2CH_3$ |
| Ia.048 | Cl | H | $CH_2CH_2CH_3$ |
| Ia.049 | H | Cl | $CH_2CH_2CH_3$ |
| Ia.050 | F | Cl | $CH_2CH_2CH_3$ |
| Ia.051 | Cl | Cl | $CH_2CH_2CH_3$ |
| Ia.052 | H | Br | $CH_2CH_2CH_3$ |
| Ia.053 | F | Br | $CH_2CH_2CH_3$ |
| Ia.054 | Cl | Br | $CH_2CH_2CH_3$ |
| Ia.055 | H | $CH_3$ | $CH_2CH_2CH_3$ |
| Ia.056 | F | $CH_3$ | $CH_2CH_2CH_3$ |
| Ia.057 | Cl | $CH_3$ | $CH_2CH_2CH_3$ |
| Ia.058 | H | CN | $CH_2CH_2CH_3$ |
| Ia.059 | F | CN | $CH_2CH_2CH_3$ |
| Ia.060 | Cl | CN | $CH_2CH_2CH_3$ |
| Ia.061 | H | H | $CH(CH_3)_2$ |
| Ia.062 | F | H | $CH(CH_3)_2$ |
| Ia.063 | Cl | H | $CH(CH_3)_2$ |
| Ia.064 | H | Cl | $CH(CH_3)_2$ |
| Ia.065 | F | Cl | $CH(CH_3)_2$ |
| Ia.066 | Cl | Cl | $CH(CH_3)_2$ |
| Ia.067 | H | Br | CH.($CH_3)_2$ |
| Ia.068 | F | Br | $CH(CH_3)_2$ |
| Ia.069 | Cl | Br | $CH(CH_3)_2$ |
| Ia.070 | H | $CH_3$ | $CH(CH_3)_2$ |
| Ia.071 | F | $CH_3$ | $CH(CH_3)_2$ |
| Ia.072 | Cl | $CH_3$ | $CH(CH_3)_2$ |
| Ia.073 | H | CN | $CH(CH_3)_2$ |
| Ia.074 | F | CN | $CH(CH_3)_2$ |
| La.075 | Cl | CN | $CH(CH_3)_2$ |
| Ia.076 | H | H | $CH_2CH_2CH_2CH_3$ |
| Ia.077 | F | H | $CH_2CH_2CH_2CH_3$ |
| Ia.078 | Cl | H | $CH_2CH_2CH_2CH_3$ |
| Ia.079 | H | Cl | $CH_2CH_2CH_2CH_3$ |
| Ia.080 | F | Cl | $CH_2CH_2CH_2CH_3$ |
| Ia.081 | Cl | Cl | $CH_2CH_2CH_2CH_3$ |
| Ia.082 | H | Br | $CH_2CH_2CH_2CH_3$ |
| Ia.083 | F | Br | $CH_2CH_2CH_2CH_3$ |
| Ia.084 | Cl | Br | $CH_2CH_2CH_2CH_3$ |
| Ia.085 | H | $CH_3$ | $CH_2CH_2CH_2CH_3$ |
| Ia.086 | F | $CH_3$ | $CH_2CH_2CH_2CH_3$ |
| Ia.087 | Cl | $CH_3$ | $CH_2CH_2CH_2CH_3$ |
| Ia.088 | H | CN | $CH_2CH_2CH_2CH_3$ |
| Ia.089 | F | CN | $CH_2CH_2CH_2CH_3$ |
| Ia.090 | Cl | CN | $CH_2CH_2CH_2CH_3$ |
| Ia.091 | H | H | $CH_2CH(CH_3)_2$ |
| Ia.092 | F | H | $CH_2CH(CH_3)_2$ |
| Ia.093 | Cl | H | $CH_2CH(CH_3)_2$ |
| Ia.094 | H | Cl | $CH_2CH(CH_3)_2$ |
| Ia.095 | F | Cl | $CH_2CH(CH_3)_2$ |
| Ia.096 | Cl | Cl | $CH_2CH(CH_3)_2$ |
| Ia.097 | H | Br | $CH_2CH(CH_3)_2$ |
| Ia.098 | F | Br | $CH_2CH(CH_3)_2$ |
| Ia.099 | Cl | Br | $CH_2CH(CH_3)_2$ |
| Ia.100 | H | $CH_3$ | $CH_2CH(CH_3)_2$ |
| Ia.101 | F | $CH_3$ | $CH_2CH(CH_3)_2$ |
| Ia.102 | Cl | $CH_3$ | $CH_2CH(CH_3)_2$ |
| Ia.103 | H | CN | $CH_2CH(CH_3)_2$ |
| Ia.104 | F | CN | $CH_2CH(CH_3)_2$ |
| Ia.105 | Cl | CN | $CH_2CH(CH_3)_2$ |
| Ia.106 | H | H | $C(CH_3)CH_2CH_3$ |
| Ia.107 | F | H | $C(CH_3)CH_2CH_3$ |
| Ia.108 | Cl | H | $C(CH_3)CH_2CH_3$ |
| Ia.109 | H | Cl | $C(CH_3)CH_2CH_3$ |
| Ia.110 | F | Cl | $C(CH_3)CH_2CH_3$ |
| Ia.111 | Cl | Cl | $C(CH_3)CH_2CH_3$ |
| Ia.112 | H | Br | $C(CH_3)CH_2CH_3$ |

TABLE 7-continued (Ia)

Structure: hexahydroisoquinoline-1,3-dione with N-aryl group (R² at one position, Cl at another), and CH=C(R⁴)—CO—O—CH₂—CO—OR⁷ substituent.

| No. | $R_2$ | $R_4$ | $R_7$ |
|---|---|---|---|
| Ia.113 | F | Br | $C(CH_3)CH_2CH_3$ |
| Ia.114 | Cl | Br | $C(CH_3)CH_2CH_3$ |
| Ia.115 | H | $CH_3$ | $C(CH_3)CH_2CH_3$ |
| Ia.116 | F | $CH_3$ | $C(CH_3)CH_2CH_3$ |
| Ia.117 | Cl | $CH_3$ | $C(CH_3)CH_2CH_3$ |
| Ia.118 | H | CN | $C(CH_3)CH_2CH_3$ |
| Ia.119 | F | CN | $C(CH_3)CH_2CH_3$ |
| Ia.120 | Cl | CN | $C(CH_3)CH_2CH_3$ |
| Ia.121 | H | H | $C(CH_3)_3$ |
| Ia.122 | F | H | $C(CH_3)_3$ |
| Ia.123 | Cl | H | $C(CH_3)_3$ |
| Ia.124 | H | Cl | $C(CH_3)_3$ |
| Ia.125 | F | Cl | $C(CH_3)_3$ |
| Ia.126 | Cl | Cl | $C(CH_3)_3$ |
| Ia.127 | H | Br | $C(CH_3)_3$ |
| Ia.128 | F | Br | $C(CH_3)_3$ |
| Ia.129 | Cl | Br | $C(CH_3)_3$ |
| Ia.130 | H | $CH_3$ | $C(CH_3)_3$ |
| Ia.131 | F | $CH_3$ | $C(CH_3)_3$ |
| Ia.132 | Cl | $CH_3$ | $C(CH_3)_3$ |
| Ia.133 | H | CN | $C(CH_3)_3$ |
| Ia.134 | F | CN | $C(CH_3)_3$ |
| Ia.135 | Cl | CN | $C(CH_3)_3$ |
| Ia.136 | H | H | $CH_2CH=CH_2$ |
| Ia.137 | F | H | $CH_2CH=CH_2$ |
| Ia.138 | Cl | H | $CH_2CH=CH_2$ |
| Ia.139 | H | Cl | $CH_2CH=CH_2$ |
| Ia.140 | F | Cl | $CH_2CH=CH_2$ |
| Ia.141 | Cl | Cl | $CH_2CH=CH_2$ |
| Ia.142 | H | Br | $CH_2CH=CH_2$ |
| Ia.143 | F | Br | $CH_2CH=CH_2$ |
| Ia.144 | Cl | Br | $CH_2CH=CH_2$ |
| Ia.145 | H | $CH_3$ | $CH_2CH=CH_2$ |
| Ia.146 | F | $CH_3$ | $CH_2CH=CH_2$ |
| Ia.147 | Cl | $CH_3$ | $CH_2CH=CH_2$ |
| Ia.148 | H | CN | $CH_2CH=CH_2$ |
| Ia.149 | F | CN | $CH_2CH=CH_2$ |
| Ia.150 | Cl | CN | $CH_2CH=CH_2$ |
| Ia.151 | H | H | $CH_2CH=CH(CH_3)$ |
| Ia.152 | F | H | $CH_2CH=CH(CH_3)$ |
| Ia.153 | Cl | H | $CH_2CH=CH(CH_3)$ |
| Ia.154 | H | Cl | $CH_2CH=CH(CH_3)$ |
| Ia.155 | F | Cl | $CH_2CH=CH(CH_3)$ |
| Ia.156 | Cl | Cl | $CH_2CH=CH(CH_3)$ |
| Ia.157 | H | Br | $CH_2CH=CH(CH_3)$ |
| Ia.158 | F | Br | $CH_2CH=CH(CH_3)$ |
| Ia.159 | Cl | Br | $CH_2CH=CH(CH_3)$ |
| Ia.160 | H | $CH_3$ | $CH_2CH=CH(CH_3)$ |
| Ia.161 | F | $CH_3$ | $CH_2CH=CH(CH_3)$ |
| Ia.162 | Cl | $CH_3$ | $CH_2CH=CH(CH_3)$ |
| Ia.163 | H | CN | $CH_2CH=CH(CH_3)$ |
| Ia.164 | F | CN | $CH_2CH=CH(CH_3)$ |
| Ia.165 | Cl | CN | $CH_2CH=CH(CH_3)$ |
| Ia.166 | H | H | $CH(CH_3)-CH=CH_2$ |
| Ia.167 | F | H | $CH(CH_3)-CH=CH_2$ |
| Ia.168 | Cl | H | $CH(CH_3)-CH=CH_2$ |
| Ia.169 | H | Cl | $CH(CH_3)-CH=CH_2$ |
| Ia.170 | F | Cl | $CH(CH_3)-CH=CH_2$ |
| Ia.171 | Cl | Cl | $CH(CH_3)-CH=CH_2$ |
| Ia.172 | H | Br | $CH(CH_3)-CH=CH_2$ |
| Ia.173 | F | Br | $CH(CH_3)-CH=CH_2$ |
| Ia.174 | Cl | Br | $CH(CH_3)-CH=CH_2$ |
| Ia.175 | H | $CH_3$ | $CH(CH_3)-CH=CH_2$ |
| Ia.176 | F | $CH_3$ | $CH(CH_3)-CH=CH_2$ |
| Ia.177 | Cl | $CH_3$ | $CH(CH_3)-CH=CH_2$ |
| Ia.178 | H | CN | $CH(CH_3)-CH=CH_2$ |
| Ia.179 | F | CN | $CH(CH_3)-CH=CH_2$ |
| Ia.180 | Cl | CN | $CH(CH_3)-CH=CH_2$ |
| Ia.181 | H | H | $CH_2-C\equiv CH$ |
| Ia.182 | F | H | $CH_2-C\equiv CH$ |
| Ia.183 | Cl | H | $CH_2-C\equiv CH$ |
| Ia.184 | H | Cl | $CH_2-C\equiv CH$ |
| Ia.185 | F | Cl | $CH_2-C\equiv CH$ |
| Ia.186 | Cl | Cl | $CH_2-C\equiv CH$ |
| Ia.187 | H | Br | $CH_2-C\equiv CH$ |
| Ia.188 | F | Br | $CH_2-C\equiv CH$ |
| Ia.189 | Cl | Br | $CH_2-C\equiv CH$ |
| Ia.190 | H | $CH_3$ | $CH_2-C\equiv CH$ |
| Ia.191 | F | $CH_3$ | $CH_2-C\equiv CH$ |
| Ia.192 | Cl | $CH_3$ | $CH_2-C\equiv CH$ |
| Ia.193 | H | CN | $CH_2-C\equiv CH$ |
| Ia.194 | F | CN | $CH_2-C\equiv CH$ |
| Ia.195 | Cl | CN | $CH_2-C\equiv CH$ |
| Ia.196 | H | H | $CH(CH_3)C\equiv CH$ |
| Ia.197 | F | H | $CH(CH_3)C\equiv CH$ |
| Ia.198 | Cl | H | $CH(CH_3)C\equiv CH$ |
| Ia.199 | H | Cl | $CH(CH_3)C\equiv CH$ |
| Ia.200 | F | Cl | $CH(CH_3)C\equiv CH$ |
| Ia.201 | Cl | Cl | $CH(CH_3)C\equiv CH$ |
| Ia.202 | H | Br | $CH(CH_3)C\equiv CH$ |
| Ia.203 | F | Br | $CH(CH_3)C\equiv CH$ |
| Ia.204 | Cl | Br | $CH(CH_3)C\equiv CH$ |
| Ia.205 | H | $CH_3$ | $CH(CH_3)C\equiv CH$ |
| Ia.206 | F | $CH_3$ | $CH(CH_3)C\equiv CH$ |
| Ia.207 | Cl | $CH_3$ | $CH(CH_3)C\equiv CH$ |
| Ia.208 | H | CN | $CH(CH_3)C\equiv CH$ |
| Ia.209 | F | CN | $CH(CH_3)C\equiv CH$ |
| Ia.210 | Cl | CN | $CH(CH_3)C\equiv CH$ |
| Ia.211 | H | H | $CH_2-C\equiv C-CH_3$ |
| Ia.212 | F | H | $CH_2-C\equiv C-CH_3$ |
| Ia.213 | Cl | H | $CH_2-C\equiv C-CH_3$ |
| Ia.214 | H | Cl | $CH_2-C\equiv C-CH_3$ |
| Ia.215 | F | Cl | $CH_2-C\equiv C-CH_3$ |
| Ia.216 | Cl | Cl | $CH_2-C\equiv C-CH_3$ |
| Ia.217 | H | Br | $CH_2-C\equiv C-CH_3$ |

TABLE 7-continued (Ia)

| No. | R₂ | R₄ | R₇ |
|---|---|---|---|
| Ia.218 | F | Br | CH₂—C≡C—CH₃ |
| Ia.219 | Cl | Br | CH₂—C≡C—CH₃ |
| Ia.220 | H | CH₃ | CH₂—C≡C—CH₃ |
| Ia.221 | F | CH₃ | CH₂—C≡C—CH₃ |
| Ia.222 | Cl | CH₃ | CH₂—C≡C—CH₃ |
| Ia.223 | H | CN | CH₂—C≡C—CH₃ |
| Ia.224 | F | CN | CH₂—C≡C—CH₃ |
| Ia.225 | Cl | CN | CH₂—C≡C—CH₃ |
| Ia.226 | H | H | CHF₂ |
| Ia.227 | F | H | CHF₂ |
| Ia.228 | Cl | H | CHF₂ |
| Ia.229 | H | Cl | CHF₂ |
| Ia.230 | F | Cl | CHF₂ |
| Ia.231 | Cl | Cl | CHF₂ |
| Ia.232 | H | Br | CHF₂ |
| Ia.233 | F | Br | CHF₂ |
| Ia.234 | Cl | Br | CHF₂ |
| Ia.235 | H | CH₃ | CHF₂ |
| Ia.236 | F | CH₃ | CHF₂ |
| Ia.237 | Cl | CH₃ | CHF₂ |
| Ia.238 | H | CN | CHF₂ |
| Ia.239 | F | CN | CHF₂ |
| Ia.240 | Cl | CN | CHF₂ |
| Ia.241 | H | H | CH₂CH₂F |
| Ia.242 | F | H | CH₂CH₂F |
| Ia.243 | Cl | H | CH₂CH₂F |
| Ia.244 | H | Cl | CH₂CH₂F |
| Ia.245 | F | Cl | CH₂CH₂F |
| Ia.246 | Cl | Cl | CH₂CH₂F |
| Ia.247 | H | Br | CH₂CH₂F |
| Ia.248 | F | Br | CH₂CH₂F |
| Ia.249 | Cl | Br | CH₂CH₂F |
| Ia.250 | H | CH₃ | CH₂CH₂F |
| Ia.251 | F | CH₃ | CH₂CH₂F |
| Ia.252 | Cl | CH₃ | CH₂CH₂F |
| Ia.253 | H | CN | CH₂CH₂F |
| Ia.254 | F | CN | CH₂CH₂F |
| Ia.255 | Cl | CN | CH₂CH₂F |
| Ia.256 | H | H | CH₂CH₂Cl |
| Ia.257 | F | H | CH₂CH₂Cl |
| Ia.258 | Cl | H | CH₂CH₂Cl |
| Ia.259 | H | Cl | CH₂CH₂Cl |
| Ia.260 | F | Cl | CH₂CH₂Cl |
| Ia.261 | Cl | Cl | CH₂CH₂Cl |
| Ia.262 | H | Br | CH₂CH₂Cl |
| Ia.263 | F | Br | CH₂CH₂Cl |
| Ia.264 | Cl | Br | CH₂CH₂Cl |
| Ia.265 | H | CH₃ | CH₂CH₂Cl |
| Ia.266 | F | CH₃ | CH₂CH₂Cl |
| Ia.267 | Cl | CH₃ | CH₂CH₂Cl |
| Ia.268 | H | CN | CH₂CH₂Cl |
| Ia.269 | F | CN | CH₂CH₂Cl |
| Ia.270 | Cl | CN | CH₂CH₂Cl |
| Ia.271 | H | H | CH₂CF₃ |
| Ia.272 | F | H | CH₂CF₃ |
| Ia.273 | Cl | H | CH₂CF₃ |
| Ia.274 | H | Cl | CH₂CF₃ |
| Ia.275 | F | Cl | CH₂CF₃ |
| Ia.276 | Cl | Cl | CH₂CF₃ |
| Ia.277 | H | Br | CH₂CF₃ |
| Ia.278 | F | Br | CH₂CF₃ |
| Ia.279 | Cl | Br | CH₂CF₃ |
| Ia.280 | H | CH₃ | CH₂CF₃ |
| Ia.281 | F | CH₃ | CH₂CF₃ |
| Ia.282 | Cl | CH₃ | CH₂CF₃ |
| Ia.283 | H | CN | CH₂CF₃ |
| Ia.284 | F | CN | CH₂CF₃ |
| Ia.285 | Cl | CN | CH₂CF₃ |
| Ia.286 | H | H | CH₂CCl₃ |
| Ia.287 | F | H | CH₂CCl₃ |
| Ia.288 | Cl | H | CH₂CCl₃ |
| Ia.289 | H | Cl | CH₂CCl₃ |
| Ia.290 | F | Cl | CH₂CCl₃ |
| Ia.291 | Cl | Cl | CH₂CCl₃ |
| Ia.292 | H | Br | CH₂CCl₃ |
| Ia.293 | F | Br | CH₂CCl₃ |
| Ia.294 | Cl | Br | CH₂CCl₃ |
| Ia.295 | H | CH₃ | CH₂CCl₃ |
| Ia.296 | F | CH₃ | CH₂CCl₃ |
| Ia.297 | Cl | CH₃ | CH₂CCl₃ |
| Ia.298 | H | CN | CH₂CCl₃ |
| Ia.299 | F | CN | CH₂CCl₃ |
| Ia.300 | Cl | CN | CH₂CCl₃ |
| Ia.301 | H | H | CH₂CN |
| Ia.302 | F | H | CH₂CN |
| Ia.303 | Cl | H | CH₂CN |
| Ia.304 | H | Cl | CH₂CN |
| Ia.305 | F | Cl | CH₂CN |
| Ia.306 | Cl | Cl | CH₂CN |
| Ia.307 | H | Br | CH₂CN |
| Ia.308 | F | Br | CH₂CN |
| Ia.309 | Cl | Br | CH₂CN |
| Ia.310 | H | CH₃ | CH₂CN |
| Ia.311 | F | CH₃ | CH₂CN |
| Ia.312 | Cl | CH₃ | CH₂CN |
| Ia.313 | H | CN | CH₂CN |
| Ia.314 | F | CN | CH₂CN |
| Ia.315 | Cl | CN | CH₂CN |
| Ia.316 | H | H | CH(CH₃)CN |
| Ia.317 | F | H | CH(CH₃)CN |
| Ia.318 | Cl | H | CH(CH₃)CN |
| Ia.319 | H | Cl | CH(CH₃)CN |
| Ia.320 | F | Cl | CH(CH₃)CN |
| Ia.321 | Cl | Cl | CH(CH₃)CN |
| Ia.322 | H | Br | CH(CH₃)CN |
| Ia.323 | F | Br | CH(CH₃)CN |
| Ia.324 | Cl | Br | CH(CH₃)CN |
| Ia.325 | H | CH₃ | CH(CH₃)CN |
| Ia.326 | F | CH₃ | CH(CH₃)CN |
| Ia.327 | Cl | CH₃ | CH(CH₃)CN |
| Ia.328 | H | CN | CH(CH₃)CN |
| Ia.329 | F | CN | CH(CH₃)CN |
| Ia.330 | Cl | CN | CH(CH₃)CN |
| Ia.331 | H | H | CH₂CH₂OCH₃ |
| Ia.332 | F | H | CH₂CH₂OCH₃ |
| Ia.333 | Cl | H | CH₂CH₂OCH₃ |
| Ia.334 | H | Cl | CH₂CH₂OCH₃ |
| Ia.335 | F | Cl | CH₂CH₂OCH₃ |
| Ia.336 | Cl | Cl | CH₂CH₂OCH₃ |
| Ia.337 | H | Br | CH₂CH₂OCH₃ |
| Ia.338 | F | Br | CH₂CH₂OCH₃ |
| Ia.339 | Cl | Br | CH₂CH₂OCH₃ |
| Ia.340 | H | CH₃ | CH₂CH₂OCH₃ |
| Ia.341 | F | CH₃ | CH₂CH₂OCH₃ |
| Ia.342 | Cl | CH₃ | CH₂CH₂OCH₃ |
| Ia.343 | H | CN | CH₂CH₂OCH₃ |
| Ia.344 | F | CN | CH₂CH₂OCH₃ |
| Ia.345 | Cl | CN | CH₂CH₂OCH₃ |
| Ia.346 | H | H | CH₂CH₂OC₂H₅ |
| Ia.347 | F | H | CH₂CH₂OC₂H₅ |
| Ia.348 | Cl | H | CH₂CH₂OCH₂CH₃ |

TABLE 7-continued (Ia)

structure: hexahydroisoquinoline-1,3-dione with N-linked 2-R²-4-Cl-phenyl bearing CH=C(R⁴)—CO—O—CH₂—CO—OR⁷

| No. | R₂ | R₄ | R₇ |
|---|---|---|---|
| Ia.349 | H | Cl | CH₂CH₂OCH₂CH₃ |
| Ia.350 | F | Cl | CH₂CH₂OCH₂CH₃ |
| Ia.351 | Cl | Cl | CH₂CH₂OCH₂CH₃ |
| Ia.352 | H | Br | CH₂CH₂OCH₂CH₃ |
| Ia.353 | F | Br | CH₂CH₂OCH₂CH₃ |
| Ia.354 | Cl | Br | CH₂CH₂OCH₂CH₃ |
| Ia.355 | H | CH₃ | CH₂CH₂OCH₂CH₃ |
| Ia.356 | F | CH₃ | CH₂CH₂OCH₂CH₃ |
| Ia.357 | Cl | CH₃ | CH₂CH₂OCH₂CH₃ |
| Ia.358 | H | CN | CH₂CH₂OCH₂CH₃ |
| Ia.359 | F | CN | CH₂CH₂OCH₂CH₃ |
| Ia.360 | Cl | CN | CH₂CH₂OCH₂CH₃ |
| Ia.361 | H | H | CH₂CH₂SCH₃ |
| Ia.362 | F | H | CH₂CH₂SCH₃ |
| Ia.363 | Cl | H | CH₂CH₂SCH₃ |
| Ia.364 | H | Cl | CH₂CH₂SCH₃ |
| Ia.365 | F | Cl | CH₂CH₂SCH₃ |
| Ia.366 | Cl | Cl | CH₂CH₂SCH₃ |
| Ia.367 | H | Br | CH₂CH₂SCH₃ |
| Ia.368 | F | Br | CH₂CH₂SCH₃ |
| Ia.369 | Cl | Br | CH₂CH₂SCH₃ |
| Ia.370 | H | CH₃ | CH₂CH₂SCH₃ |
| Ia.371 | F | CH₃ | CH₂CH₂SCH₃ |
| Ia.372 | Cl | CH₃ | CH₂CH₂SCH₃ |
| Ia.373 | H | CN | CH₂CH₂SCH₃ |
| Ia.374 | F | CN | CH₂CH₂SCH₃ |
| Ia.375 | Cl | CN | CH₂CH₂SCH₃ |
| Ia.376 | H | H | CH₂CH₂SCH₂CH₃ |
| Ia.377 | F | H | CH₂CH₂SCH₂CH₃ |
| Ia.378 | Cl | H | CH₂CH₂SCH₂CH₃ |
| Ia.379 | H | Cl | CH₂CH₂SCH₂CH₃ |
| Ia.380 | F | Cl | CH₂CH₂SCH₂CH₃ |
| Ia.381 | Cl | Cl | CH₂CH₂SCH₂CH₃ |
| Ia.382 | H | Br | CH₂CH₂SCH₂CH₃ |
| Ia.383 | F | Br | CH₂CH₂SCH₂CH₃ |
| Ia.384 | Cl | Br | CH₂CH₂SCH₂CH₃ |
| Ia.385 | H | CH₃ | CH₂CH₂SCH₂CH₃ |
| Ia.386 | F | CH₃ | CH₂CH₂SCH₂CH₃ |
| Ia.387 | Cl | CH₃ | CH₂CH₂SCH₂CH₃ |
| Ia.388 | H | CN | CH₂CH₂SCH₂CH₃ |
| Ia.389 | F | CN | CH₂CH₂SCH₂CH₃ |
| Ia.390 | Cl | CN | CH₂CH₂SCH₂CH₃ |
| Ia.391 | H | H | CH₂CO₂CH₃ |
| Ia.392 | F | H | CH₂CO₂CH₃ |
| Ia.393 | Cl | H | CH₂CO₂CH₃ |
| Ia.394 | H | Cl | CH₂CO₂CH₃ |
| Ia.395 | F | Cl | CH₂CO₂CH₃ |
| Ia.396 | Cl | Cl | CH₂CO₂CH₃ |
| Ia.397 | H | Br | CH₂CO₂CH₃ |
| Ia.398 | F | Br | CH₂CO₂CH₃ |
| Ia.399 | Cl | Br | CH₂CO₂CH₃ |
| Ia.400 | H | CH₃ | CH₂CO₂CH₃ |
| Ia.401 | F | CH₃ | CH₂CO₂CH₃ |
| Ia.402 | Cl | CH₃ | CH₂CO₂CH₃ |
| Ia.403 | H | CN | CH₂CO₂CH₃ |
| Ia.404 | F | CN | CH₂CO₂CH₃ |
| Ia.405 | Cl | CN | CH₂CO₂CH₃ |
| Ia.406 | H | H | CH(CH₃)CO₂CH₂CH₃ |
| Ia.407 | F | H | CH(CH₃)CO₂CH₂CH₃ |
| Ia.408 | Cl | H | CH(CH₃)CO₂CH₂CH₃ |
| Ia.409 | H | Cl | CH(CH₃)CO₂CH₂CH₃ |
| Ia.410 | F | Cl | CH(CH₃)CO₂CH₂CH₃ |
| Ia.411 | Cl | Cl | CH(CH₃)CO₂CH₂CH₃ |
| Ia.412 | H | Br | CH(CH₃)CO₂CH₂CH₃ |
| Ia.413 | F | Br | CH(CH₃)CO₂CH₂CH₃ |
| Ia.414 | Cl | Br | CH(CH₃)CO₂CH₂CH₃ |
| Ia.415 | H | CH₃ | CH(CH₃)CO₂CH₂CH₃ |
| Ia.416 | F | CH₃ | CH(CH₃)CO₂CH₂CH₃ |
| Ia.417 | Cl | CH₃ | CH(CH₃)CO₂CH₂CH₃ |
| Ia.418 | H | CN | CH(CH₃)CO₂CH₂CH₃ |
| Ia.419 | F | CN | CH(CH₃)CO₂CH₂CH₃ |
| Ia.420 | Cl | CN | CH(CH₃)CO₂CH₂CH₃ |
| Ia.421 | H | H | cyclopropyl |
| Ia.422 | F | H | cyclopropyl |
| Ia.423 | Cl | H | cyclopropyl |
| Ia.424 | H | Cl | cyclopropyl |
| Ia.425 | F | Cl | cyclopropyl |
| Ia.426 | Cl | Cl | cyclopropyl |
| Ia.427 | H | Br | cyclopropyl |
| Ia.428 | F | Br | cyclopropyl |
| Ia.429 | Cl | Br | cyclopropyl |
| Ia.430 | H | CH₃ | cyclopropyl |
| Ia.431 | F | CH₃ | cyclopropyl |
| Ia.432 | Cl | CH₃ | cyclopropyl |
| Ia.433 | H | CN | cyclopropyl |
| Ia.434 | F | CN | cyclopropyl |
| Ia.435 | Cl | CN | cyclopropyl |
| Ia.436 | H | H | CH₂-cyclopropyl |
| Ia.437 | F | H | CH₂-cyclopropyl |
| Ia.438 | Cl | H | CH₂-cyclopropyl |
| Ia.439 | H | Cl | CH₂-cyclopropyl |
| Ia.440 | F | Cl | CH₂-cyclopropyl |
| Ia.441 | Cl | Cl | CH₂-cyclopropyl |
| Ia.442 | H | Br | CH₂-cyclopropyl |
| Ia.443 | F | Br | CH₂-cyclopropyl |
| Ia.444 | Cl | Br | CH₂-cyclopropyl |
| Ia.445 | H | CH₃ | CH₂-cyclopropyl |
| Ia.446 | F | CH₃ | CH₂-cyclopropyl |
| Ia.447 | Cl | CH₃ | CH₂-cyclopropyl |
| Ia.448 | H | CN | CH₂-cyclopropyl |
| Ia.449 | F | CN | CH₂-cyclopropyl |
| Ia.450 | Cl | CN | CH₂-cyclopropyl |
| Ia.451 | H | H | phenyl |
| Ia.452 | F | H | phenyl |
| Ia.453 | Cl | H | phenyl |
| Ia.454 | H | Cl | phenyl |
| Ia.455 | F | Cl | phenyl |
| Ia.456 | Cl | Cl | phenyl |
| Ia.457 | H | Br | phenyl |
| Ia.458 | F | Br | phenyl |
| Ia.459 | Cl | Br | phenyl |
| Ia.460 | H | CH₃ | phenyl |
| Ia.461 | F | CH₃ | phenyl |
| Ia.462 | Cl | CH₃ | phenyl |
| Ia.463 | H | CN | phenyl |
| Ia.464 | F | CN | phenyl |
| Ia.465 | Cl | CN | phenyl |
| Ia.466 | H | H | 2-F-phenyl |
| Ia.467 | F | H | 2-F-phenyl |
| Ia.468 | Cl | H | 2-F-phenyl |
| Ia.469 | H | Cl | 2-F-phenyl |
| Ia.470 | F | Cl | 2-F-phenyl |
| Ia.471 | Cl | Cl | 2-F-phenyl |
| Ia.472 | H | Br | 2-F-phenyl |
| Ia.473 | F | Br | 2-F-phenyl |
| Ia.474 | Cl | Br | 2-F-phenyl |
| Ia.475 | H | CH₃ | 2-F-phenyl |
| Ia.476 | F | CH₃ | 2-F-phenyl |
| Ia.477 | Cl | CH₃ | 2-F-phenyl |
| Ia.478 | H | CN | 2-F-phenyl |
| Ia.479 | F | CN | 2-F-phenyl |
| Ia.480 | Cl | CN | 2-F-phenyl |
| Ia.481 | H | H | 3-F-phenyl |
| Ia.482 | F | H | 3-F-phenyl |
| Ia.483 | Cl | H | 3-F-phenyl |
| Ia.484 | H | Cl | 3-F-phenyl |
| Ia.485 | F | Cl | 3-F-phenyl |
| Ia.486 | Cl | Cl | 3-F-phenyl |

TABLE 7-continued (Ia)

Structure: tetrahydroisoquinoline-1,3-dione N-substituted with phenyl bearing R², Cl, and CH=C(R⁴)—CO—O—CH₂—CO—OR⁷

| No. | R₂ | R₄ | R₇ |
|---|---|---|---|
| Ia.487 | H | Br | 3-F-phenyl |
| Ia.488 | F | Br | 3-F-phenyl |
| Ia.489 | Cl | Br | 3-F-phenyl |
| Ia.490 | H | CH₃ | 3-F-phenyl |
| Ia.491 | F | CH₃ | 3-F-phenyl |
| Ia.492 | Cl | CH₃ | 3-F-phenyl |
| Ia.493 | H | CN | 3-F-phenyl |
| Ia.494 | F | CN | 3-F-phenyl |
| Ia.495 | Cl | CN | 3-F-phenyl |
| Ia.496 | H | H | 4-F-phenyl |
| Ia.497 | F | H | 4-F-phenyl |
| Ia.498 | Cl | H | 4-F-phenyl |
| Ia.499 | H | Cl | 4-F-phenyl |
| Ia.500 | F | Cl | 4-F-phenyl |
| Ia.501 | Cl | Cl | 4-F-phenyl |
| Ia.502 | H | Br | 4-F-phenyl |
| Ia.503 | F | Br | 4-F-phenyl |
| Ia.504 | Cl | Br | 4-F-phenyl |
| Ia.505 | H | CH₃ | 4-F-phenyl |
| Ia.506 | F | CH₃ | 4-F-phenyl |
| Ia.507 | Cl | CH₃ | 4-F-phenyl |
| Ia.508 | H | CN | 4-F-phenyl |
| Ia.509 | F | CN | 4-F-phenyl |
| Ia.510 | Cl | CN | 4-F-phenyl |
| Ia.511 | H | H | 2-Cl-phenyl |
| Ia.512 | F | H | 2-Cl-phenyl |
| Ia.513 | Cl | H | 2-Cl-phenyl |
| Ia.514 | H | Cl | 2-Cl-phenyl |
| Ia.515 | F | Cl | 2-Cl-phenyl |
| Ia.516 | Cl | Cl | 2-Cl-phenyl |
| Ia.517 | H | Br | 2-Cl-phenyl |
| Ia.518 | F | Br | 2-Cl-phenyl |
| Ia.519 | Cl | Br | 2-Cl-phenyl |
| Ia.520 | H | CH₃ | 2-Cl-phenyl |
| Ia.521 | F | CH₃ | 2-Cl-phenyl |
| Ia.522 | Cl | CH₃ | 2-Cl-phenyl |
| Ia.523 | H | CN | 2-Cl-phenyl |
| Ia.524 | F | CN | 2-Cl-phenyl |
| Ia.525 | Cl | CN | 2-Cl-phenyl |
| Ia.526 | H | H | 3-Cl-phenyl |
| Ia.527 | F | H | 3-Cl-phenyl |
| Ia.528 | Cl | H | 3-Cl-phenyl |
| Ia.529 | H | Cl | 3-Cl-phenyl |
| Ia.530 | F | Cl | 3-Cl-phenyl |
| Ia.531 | Cl | Cl | 3-Cl-phenyl |
| Ia.532 | H | Br | 3-Cl-phenyl |
| Ia.533 | F | Br | 3-Cl-phenyl |
| Ia.534 | Cl | Br | 3-Cl-phenyl |
| Ia.535 | H | CH₃ | 3-Cl-phenyl |
| Ia.536 | F | CH₃ | 3-Cl-phenyl |
| Ia.537 | Cl | CH₃ | 3-Cl-phenyl |
| Ia.538 | H | CN | 3-Cl-phenyl |
| Ia.539 | F | CN | 3-Cl-phenyl |
| Ia.540 | Cl | CN | 3-Cl-phenyl |
| Ia.541 | H | H | 4-Cl-phenyl |
| Ia.542 | F | H | 4-Cl-phenyl |
| Ia.543 | Cl | H | 4-Cl-phenyl |
| Ia.544 | H | Cl | 4-Cl-phenyl |
| Ia.545 | F | Cl | 4-Cl-phenyl |
| Ia.546 | Cl | Cl | 4-Cl-phenyl |
| Ia.547 | H | Br | 4-Cl-phenyl |
| Ia.548 | F | Br | 4-Cl-phenyl |
| Ia.549 | Cl | Br | 4-Cl-phenyl |
| Ia.550 | H | CH₃ | 4-Cl-phenyl |
| Ia.551 | F | CH₃ | 4-Cl-phenyl |
| Ia.552 | Cl | CH₃ | 4-Cl-phenyl |
| Ia.553 | H | CN | 4-Cl-phenyl |
| Ia.554 | F | CN | 4-Cl-phenyl |
| Ia.555 | Cl | CN | 4-Cl-phenyl |
| Ia.556 | H | H | 2-CH₃-phenyl |
| Ia.557 | F | H | 2-CH₃-phenyl |
| Ia.558 | Cl | H | 2-CH₃-phenyl |
| Ia.559 | H | Cl | 2-CH₃-phenyl |
| Ia.560 | F | Cl | 2-CH₃-phenyl |
| Ia.561 | Cl | Cl | 2-CH₃-phenyl |
| Ia.562 | H | Br | 2-CH₃-phenyl |
| Ia.563 | F | Br | 2-CH₃-phenyl |
| Ia.564 | Cl | Br | 2-CH₃-phenyl |
| Ia.565 | H | CH₃ | 2-CH₃-phenyl |
| Ia.566 | F | CH₃ | 2-CH₃-phenyl |
| Ia.567 | Cl | CH₃ | 2-CH₃-phenyl |
| Ia.568 | H | CN | 2-CH₃-phenyl |
| Ia.569 | F | CN | 2-CH₃-phenyl |
| Ia.570 | Cl | CN | 2-CH₃-phenyl |
| Ia.571 | H | H | 3-CH₃-phenyl |
| Ia.572 | F | H | 3-CH₃-phenyl |
| Ia.573 | Cl | H | 3-CH₃-phenyl |
| Ia.574 | H | Cl | 3-CH₃-phenyl |
| Ia.575 | F | Cl | 3-CH₃-phenyl |
| Ia.576 | Cl | Cl | 3-CH₃-phenyl |
| Ia.577 | H | Br | 3-CH₃-phenyl |
| Ia.578 | F | Br | 3-CH₃-phenyl |
| Ia.579 | Cl | Br | 3-CH₃-phenyl |
| Ia.580 | H | CH₃ | 3-CH₃-phenyl |
| Ia.581 | F | CH₃ | 3-CH₃-phenyl |
| Ia.582 | Cl | CH₃ | 3-CH₃-phenyl |
| Ia.583 | H | CN | 3-CH₃-phenyl |
| Ia.584 | F | CN | 3-CH₃-phenyl |
| Ia.585 | Cl | CN | 3-CH₃-phenyl |
| Ia.586 | H | H | 4-CH₃-phenyl |
| Ia.587 | F | H | 4-CH₃-phenyl |
| Ia.588 | Cl | H | 4-CH₃-phenyl |
| Ia.589 | H | Cl | 4-CH₃-phenyl |
| Ia.590 | F | Cl | 4-CH₃-phenyl |
| Ia.591 | Cl | Cl | 4-CH₃-phenyl |
| Ia.592 | H | Br | 4-CH₃-phenyl |
| Ia.593 | F | Br | 4-CH₃-phenyl |
| Ia.594 | Cl | Br | 4-CH₃-phenyl |
| Ia.595 | H | CH₃ | 4-CH₃-phenyl |
| Ia.596 | F | CH₃ | 4-CH₃-phenyl |
| Ia.597 | Cl | CH₃ | 4-CH₃-phenyl |
| Ia.598 | H | CN | 4-CH₃-phenyl |
| Ia.599 | F | CN | 4-CH₃-phenyl |
| Ia.600 | Cl | CN | 4-CH₃-phenyl |
| Ia.601 | H | H | 2-CF₃-phenyl |
| Ia.602 | F | H | 2-CF₃-phenyl |
| Ia.603 | Cl | H | 2-CF₃-phenyl |
| Ia.604 | H | Cl | 2-CF₃-phenyl |
| Ia.605 | F | Cl | 2-CF₃-phenyl |
| Ia.606 | Cl | Cl | 2-CF₃-phenyl |
| Ia.607 | H | Br | 2-CF₃-phenyl |
| Ia.608 | F | Br | 2-CF₃-phenyl |
| Ia.609 | Cl | Br | 2-CF₃-phenyl |
| Ia.610 | H | CH₃ | 2-CF₃-phenyl |
| Ia.611 | F | CH₃ | 2-CF₃-phenyl |
| Ia.612 | Cl | CH | 2-CF₃-phenyl |
| Ia.613 | H | CN | 2-CF₃-phenyl |
| Ia.614 | F | CN | 2-CF₃-phenyl |
| Ia.615 | Cl | CN | 2-CF₃-phenyl |
| Ia.616 | H | H | 3-CF₃-phenyl |
| Ia.617 | F | H | 3-CF₃-phenyl |
| Ia.618 | Cl | H | 3-CF₃-phenyl |
| Ia.619 | H | Cl | 3-CF₃-phenyl |
| Ia.620 | F | Cl | 3-CF₃-phenyl |
| Ia.621 | Cl | Cl | 3-CF₃-phenyl |
| Ia.622 | H | Br | 3-CF₃-phenyl |
| Ia.623 | F | Br | 3-CF₃-phenyl |
| Ia.624 | Cl | Br | 3-CF₃-phenyl |

TABLE 7-continued (Ia)

Structure: tetrahydroisoindole-1,3-dione N-substituted with phenyl bearing $R^2$, Cl, and CH=C($R^4$)—CO—O—CH$_2$—CO—OR$^7$

| No. | R$_2$ | R$_4$ | R$_7$ |
| --- | --- | --- | --- |
| Ia.625 | H | CH$_3$ | 3-CF$_3$-phenyl |
| Ia.626 | F | CH$_3$ | 3-CF$_3$-phenyl |
| Ia.627 | Cl | CH$_3$ | 3-CF$_3$-phenyl |
| Ia.628 | H | CN | 3-CF$_3$-phenyl |
| Ia.629 | F | CN | 3-CF$_3$-phenyl |
| Ia.630 | Cl | CN | 3-CF$_3$-phenyl |
| Ia.631 | H | H | 4-CF$_3$-phenyl |
| Ia.632 | F | H | 4-CF$_3$-phenyl |
| Ia.633 | Cl | H | 4-CF$_3$-phenyl |
| Ia.634 | H | Cl | 4-CF$_3$-phenyl |
| Ia.635 | F | Cl | 4-CF$_3$-phenyl |
| Ia.636 | Cl | Cl | 4-CF$_3$-phenyl |
| Ia.637 | H | Br | 4-CF$_3$-phenyl |
| Ia.638 | F | Br | 4-CF$_3$-phenyl |
| Ia.639 | Cl | Br | 4-CF$_3$-phenyl |
| Ia.640 | H | CH$_3$ | 4-CF$_3$-phenyl |
| Ia.641 | F | CH$_3$ | 4-CF$_3$-phenyl |
| Ia.642 | Cl | CH$_3$ | 4-CF$_3$-phenyl |
| Ia.643 | H | CN | 4-CF$_3$-phenyl |
| Ia.644 | F | CN | 4-CF$_3$-phenyl |
| Ia.645 | Cl | CN | 4-CF$_3$-phenyl |
| Ia.646 | H | H | 2-CH$_3$O-phenyl |
| Ia.647 | F | H | 2-CH$_3$O-phenyl |
| Ia.648 | Cl | H | 2-CH$_3$O-phenyl |
| Ia.649 | H | Cl | 2-CH$_3$O-phenyl |
| Ia.650 | F | Cl | 2-CH$_3$O-phenyl |
| Ia.651 | Cl | Cl | 2-CH$_3$O-phenyl |
| Ia.652 | H | Br | 2-CH$_3$O-phenyl |
| Ia.653 | F | Br | 2-CH$_3$O-phenyl |
| Ia.654 | Cl | Br | 2-CH$_3$O-phenyl |
| Ia.655 | H | CH$_3$ | 2-CH$_3$O-phenyl |
| Ia.656 | F | CH$_3$ | 2-CH$_3$O-phenyl |
| Ia.657 | Cl | CH$_3$ | 2-CH$_3$O-phenyl |
| Ia.658 | H | CN | 2-CH$_3$O-phenyl |
| Ia.659 | F | CN | 2-CH$_3$O-phenyl |
| Ia.660 | Cl | CN | 2-CH$_3$O-phenyl |
| Ia.661 | H | H | 3-CH$_3$O-phenyl |
| Ia.662 | F | H | 3-CH$_3$O-phenyl |
| Ia.663 | Cl | H | 3-CH$_3$O-phenyl |
| Ia.664 | H | Cl | 3-CH$_3$O-phenyl |
| Ia.665 | F | Cl | 3-CH$_3$O-phenyl |
| Ia.666 | Cl | Cl | 3-CH$_3$O-phenyl |
| Ia.667 | H | Br | 3-CH$_3$O-phenyl |
| Ia.668 | F | Br | 3-CH$_3$O-phenyl |
| Ia.669 | Cl | Br | 3-CH$_3$O-phenyl |
| Ia.670 | H | CH$_3$ | 3-CH$_3$O-phenyl |
| Ia.671 | F | CH$_3$ | 3-CH$_3$O-phenyl |
| Ia.672 | Cl | CH$_3$ | 3-CH$_3$O-phenyl |
| Ia.673 | H | CN | 3-CH$_3$O-phenyl |
| Ia.674 | F | CN | 3-CH$_3$O-phenyl |
| Ia.675 | Cl | CN | 3-CH$_3$O-phenyl |
| Ia.676 | H | H | 4-CH$_3$O-phenyl |
| Ia.677 | F | H | 4-CH$_3$O-phenyl |
| Ia.678 | Cl | H | 4-CH$_3$O-phenyl |
| Ia.679 | H | Cl | 4-CH$_3$O-phenyl |
| Ia.680 | F | Cl | 4-CH$_3$O-phenyl |
| Ia.681 | Cl | Cl | 4-CH$_3$O-phenyl |
| Ia.682 | H | Br | 4-CH$_3$O-phenyl |
| Ia.683 | F | Br | 4-CH$_3$O-phenyl |
| Ia.684 | Cl | Br | 4-CH$_3$O-phenyl |
| Ia.685 | H | CH$_3$ | 4-CH$_3$O-phenyl |
| Ia.686 | F | CH$_3$ | 4-CH$_3$O-phenyl |
| Ia.687 | Cl | CH$_3$ | 4-CH$_3$O-phenyl |
| Ia.688 | H | CN | 4-CH$_3$O-phenyl |
| Ia.689 | F | CN | 4-CH$_3$O-phenyl |
| Ia.690 | Cl | CN | 4-CH$_3$O-phenyl |
| Ia.691 | H | H | 2-CO$_2$CH$_3$-phenyl |
| Ia.692 | F | H | 2-CO$_2$CH$_3$-phenyl |
| Ia.693 | Cl | H | 2-CO$_2$CH$_3$-phenyl |
| Ia.694 | H | Cl | 2-CO$_2$CH$_3$-phenyl |
| Ia.695 | F | Cl | 2-CO$_2$CH$_3$-phenyl |
| Ia.696 | Cl | Cl | 2-CO$_2$CH$_3$-phenyl |
| Ia.697 | H | Br | 2-CO$_2$CH$_3$-phenyl |
| Ia.698 | F | Br | 2-CO$_2$CH$_3$-phenyl |
| Ia.699 | Cl | Br | 2-CO$_2$CH$_3$-phenyl |
| Ia.700 | H | CH$_3$ | 2-CO$_2$CH$_3$-phenyl |
| Ia.701 | F | CH$_3$ | 2-CO$_2$CH$_3$-phenyl |
| Ia.702 | Cl | CH$_3$ | 2-CO$_2$CH$_3$-phenyl |
| Ia.703 | H | CN | 2-CO$_2$CH$_3$-phenyl |
| Ia.704 | F | CN | 2-CO$_2$CH$_3$-phenyl |
| Ia.705 | Cl | CN | 2-CO$_2$CH$_3$-phenyl |
| Ia.706 | H | H | 3-CO$_2$CH$_3$-phenyl |
| Ia.707 | F | H | 3-CO$_2$CH$_3$-phenyl |
| Ia.708 | Cl | H | 3-CO$_2$CH$_3$-phenyl |
| Ia.709 | H | Cl | 3-CO$_2$CH$_3$-phenyl |
| Ia.710 | F | Cl | 3-CO$_2$CH$_3$-phenyl |
| Ia.711 | Cl | Cl | 3-CO$_2$CH$_3$-phenyl |
| Ia.712 | H | Br | 3-CO$_2$CH$_3$-phenyl |
| Ia.713 | F | Br | 3-CO$_2$CH$_3$-phenyl |
| Ia.714 | Cl | Br | 3-CO$_2$CH$_3$-phenyl |
| Ia.715 | H | CH$_3$ | 3-CO$_2$CH$_3$-phenyl |
| Ia.716 | F | CH$_3$ | 3-CO$_2$CH$_3$-phenyl |
| Ia.717 | Cl | CH$_3$ | 3-CO$_2$CH$_3$-phenyl |
| Ia.718 | H | CN | 3-CO$_2$CH$_3$-phenyl |
| Ia.719 | F | CN | 3-CO$_2$CH$_3$-phenyl |
| Ia.720 | Cl | CN | 3-CO$_2$CH$_3$-phenyl |
| Ia.721 | H | H | 4-CO$_2$CH$_3$-phenyl |
| Ia.722 | F | H | 4-CO$_2$CH$_3$-phenyl |
| Ia.723 | Cl | H | 4-CO$_2$CH$_3$-phenyl |
| Ia.724 | H | Cl | 4-CO$_2$CH$_3$-phenyl |
| Ia.725 | F | Cl | 4-CO$_2$CH$_3$-phenyl |
| Ia.726 | Cl | Cl | 4-CO$_2$CH$_3$-phenyl |
| Ia.727 | H | Br | 4-CO$_2$CH$_3$-phenyl |
| Ia.728 | F | Br | 4-CO$_2$CH$_3$-phenyl |
| Ia.729 | Cl | Br | 4-CO$_2$CH$_3$-phenyl |
| Ia.730 | H | CH$_3$ | 4-CO$_2$CH$_3$-phenyl |
| Ia.731 | F | CH$_3$ | 4-CO$_2$CH$_3$-phenyl |
| Ia.732 | Cl | CH$_3$ | 4-CO$_2$CH$_3$-phenyl |
| Ia.733 | H | CN | 4-CO$_2$CH$_3$-phenyl |
| Ia.734 | F | CN | 4-CO$_2$CH$_3$-phenyl |
| Ia.735 | Cl | CN | 4-CO$_2$CH$_3$-phenyl |
| Ia.736 | H | H | CH$_2$-phenyl |
| Ia.737 | F | H | CH$_2$-phenyl |
| Ia.738 | Cl | H | CH$_2$-phenyl |
| Ia.739 | H | Cl | CH$_2$-phenyl |
| Ia.740 | F | Cl | CH$_2$-phenyl |
| Ia.741 | Cl | Cl | CH$_2$-phenyl |
| Ia.742 | H | Br | CH$_2$-phenyl |
| Ia.743 | F | Br | CH$_2$-phenyl |
| Ia.744 | Cl | Br | CH$_2$-phenyl |
| Ia.745 | H | CH$_3$ | CH$_2$-phenyl |
| Ia.746 | F | CH$_3$ | CH$_2$-phenyl |
| Ia.747 | Cl | CH$_3$ | CH$_2$-phenyl |
| Ia.748 | H | CN | CH$_2$-phenyl |
| Ia.749 | F | CN | CH$_2$-phenyl |
| Ia.750 | Cl | CN | CH$_2$-phenyl |

Furthermore, the following substituted cinnamic acid derivatives of the formula I are particularly preferred:

the compounds Ib0.001–Ib0.750, which differ from the corresponding compounds Ia0.001–Ia0.750 in that $R^6$ is methyl:

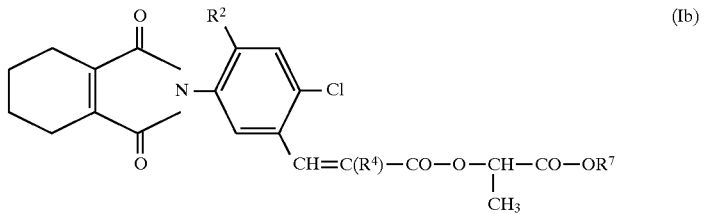

(Ib)

the compounds Ic0.001–Ic0.750, which differ from the corresponding compounds Ia0.001–Ia0.750 in that $R^6$ is ethyl:

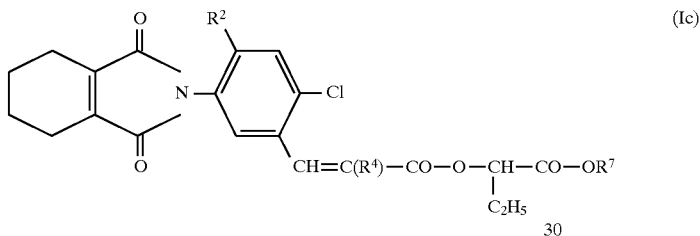

(Ic)

the compounds Id0.001–Id0.750, which differ from the corresponding compounds Ia0.001–Ia0.750 in that $R^6$ is isopropyl;

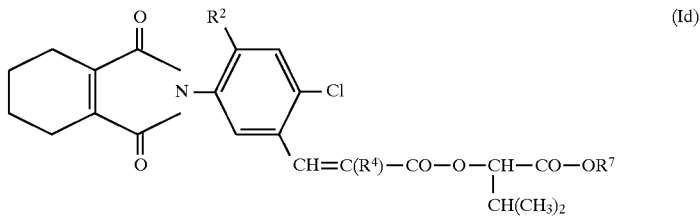

(Id)

the compounds Ie0.001–Ie0.750, which differ from the corresponding compounds Ia0.001–Ia0.750 in that $R^6$ is cyclopropyl;

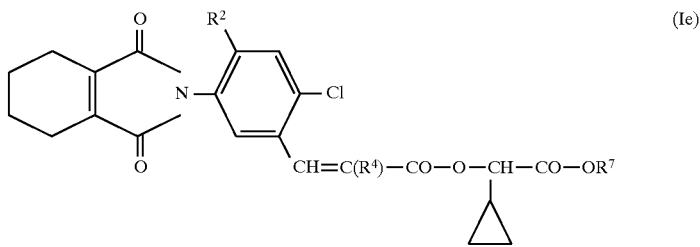

(Ie)

the compounds If0.001–If0.750, which differ from the corresponding compounds Ia0.001–Ia0.750 in that $R^5$ and $R^6$ are each methyl;

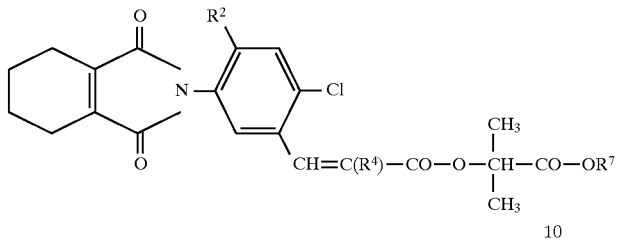

(If)

the compounds Ig0.001–Ig0.750, which differ from the corresponding compounds Ia0.001–Ia0.750 in that $R^5$ is ethoxy;

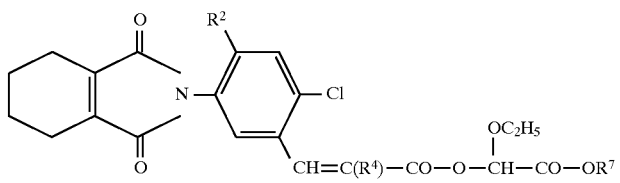

(Ig)

the compounds Ih0.001–Ih0.750, which differ from the corresponding compounds Ia0.001–Ia0.750 in that X is NH:

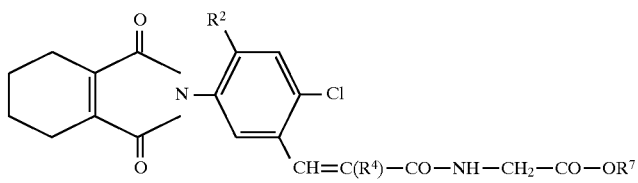

(Ih)

the compounds Ii0.001–Ii0.750, which differ from the corresponding compounds Ia0.001–Ia0.750 in that X is NH and $R^6$ is methyl:

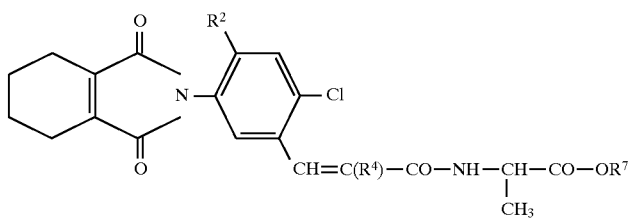

(Ii)

the compounds Ik0.001–Ik0.750, which differ from the corresponding compounds Ia0.001–Ia0.750 in that X is NH and $R^6$ is isopropyl:

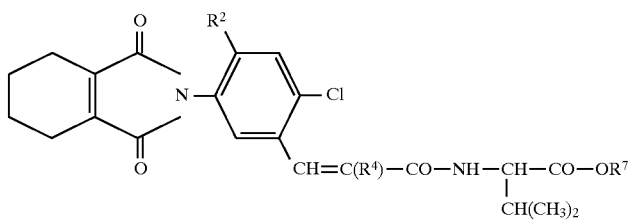

(Ik)

the compounds Il0.001–Il0.750, which differ from the corresponding compounds Ia0.001–Ia0.750 in that X is NH and $R^6$ is 2-methylpropyl:

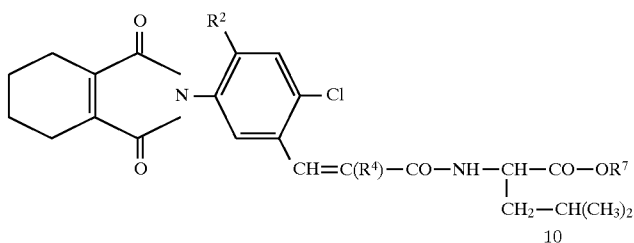
(II)

the compounds Im0.001–Im0.750, which differ from the corresponding compounds Ia0.001–Ia0.750 in that X is NH and $R^6$ is 2-methylthioethyl:

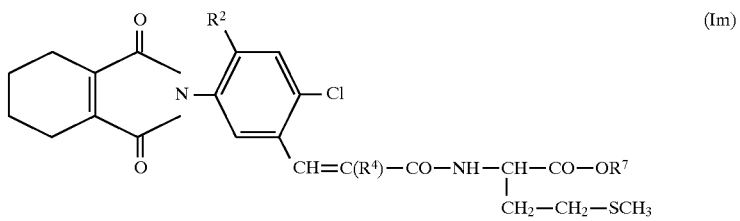
(Im)

the compounds In0.001–In0.750, which differ from the corresponding compounds Ia0.001–Ia0.750 in that X is NH and $R^6$ is benzyl;

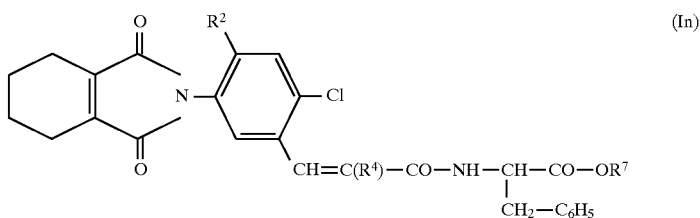
(In)

the compounds Io0.001–Io0.750, which differ from the corresponding compounds Ia0.001–Ia0.750 in that X is $N(CH_3)$:

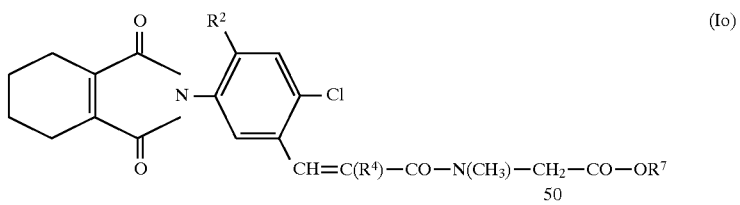
(Io)

the compounds Ip0.001–Ip0.750, which differ from the corresponding compounds Ia0.001–Ia0.750 in that X is $N(R^8)$ and $R^8$ together with $R^6$ forms a propylene chain:

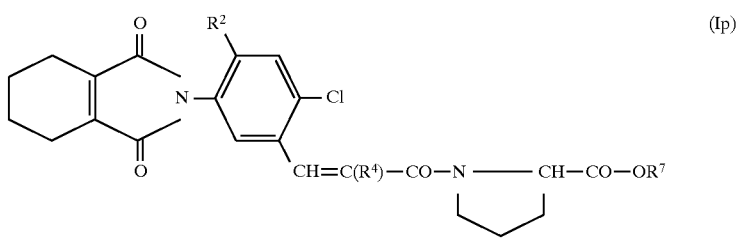
(Ip)

The substituted phthalimidocinnamic acid derivatives of the formula I are obtainable by various methods, for example by one of the following processes:

Process A:

Diazotization of anilines III and reaction of the resulting diazonium salts with propynoic acid derivatives IV in a manner known per se (cf. N. I. Granushchak et al., Zh. Organ. Ximii. (1980) 16 HO12, 2578–2581) by the Meerwein method or modifications thereof:

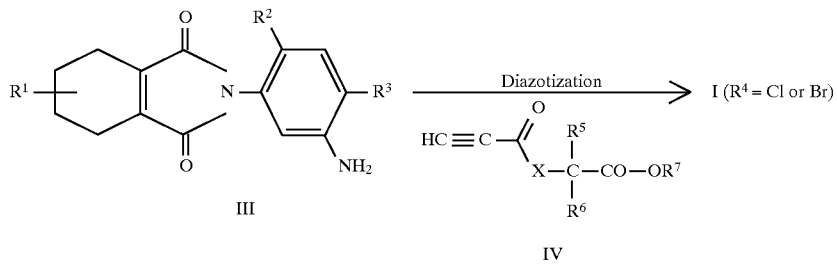

In this method, the aniline III is first converted into a suitable diazonium salt, which is then reacted with IV in the presence of a copper salt.

The phenyldiazonium salt is advantageously prepared by reacting the aniline III in an aqueous acid solution, for example in hydrochloric acid, hydrobromic acid or sulfuric acid, with a nitrite, such as sodium nitrite or potassium nitrite, and reacting the product with the propynoic acid derivative IV in an inert solvent in the presence of a copper halide, such as copper(I) chloride, copper(I) bromide, copper(II) chloride or copper(II) bromide.

Examples of suitable inert solvents are water, acetonitrile, ketones, such as acetone, diethyl ketone and methyl ethyl ketone, ethers, such as dioxane and tetrahydrofuran, and alcohols, such as methanol and ethanol.

A further possibility for the preparation of the phenyldiazonium salt is to react the aniline III in an anhydrous system, for example in glacial acetic acid which contains hydrogen chloride, in dioxane, absolute ethanol, tetrahydrofuran or acetonitrile or in acetone, with a nitrite, such as tert-butyl nitrite or isopentyl nitrite. In this case, the diazotization can take place in the presence of the propynoic acid derivative IV and of the copper halide.

The reaction temperature is usually from −30° to 80° C.

The components of the diazotization reaction are usually used in a roughly stoichiometric ratio, but an excess of one of the components may be advantageous, for example to ensure as complete conversion as possible of the other component.

The propynoic acid derivative IV can be used in equimolar amounts, in excess or in less than the stoichiometric amount, based on the phenyldiazonium salt. In general, a large excess, based on the phenyldiazonium salt, of propynoic acid derivative IV has proven particularly advantageous.

The copper halide is usually used in a stoichiometric ratio, but an excess or less than the stoichiometric amount is also possible.

Process B:

Reaction of a benzaldehyde V with an ylide VI in a manner known per se (cf. for example R. S. Mali and V. J. Yadav, Synthesis (1984) 10, 862):

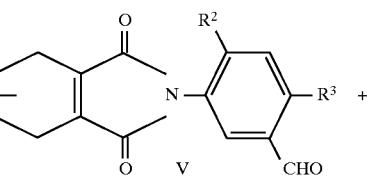

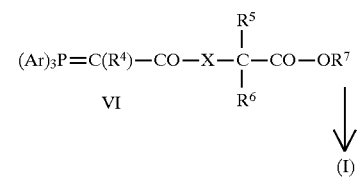

Ar is an aromatic radical which, if desired, may be substituted, preferably phenyl.

Examples of suitable solvents are aromatic hydrocarbons, such as benzene and toluene, ethers, such as diethyl ether, tetrahydrofuran and dioxane, dipolar aprotic solvents, such as dimethyl sulfoxide and dimethylformamide, and protic solvents, such as methanol and ethanol. Mixtures of the stated solvents are also suitable.

The reaction is usually carried out at from 0° C. to the boiling point of the particular reaction mixture.

Usually, the benzaldehyde and the ylide are used in roughly stoichiometric amounts, but it is also possible to use an excess of one of the components.

Process C:

Reaction of a benzaldehyde V with a CH-acidic compound VII in a manner known per se (cf. for example J. March, Advanced Organic Chemistry, page 835 et seq.):

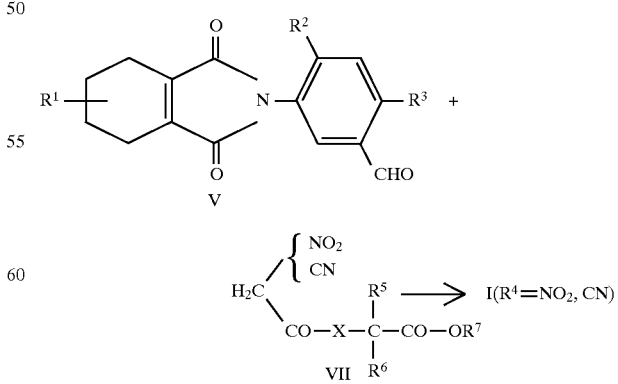

Depending on the particular substituents and on the reaction conditions, it may be advantageous to carry out the reaction in the presence of a catalytic or roughly equivalent amount, based on VII, of a base or in the presence of an acid.

Examples of suitable bases are alkali metal alcoholates, such as sodium methylate, sodium ethylate and potassium tert-butylate, aromatic and aliphatic nitrogen bases, such as pyridine, piperidine, triethylamine, ammonium acetate and β-alanine, and metal hydrides such as sodium hydride and potassium hydride.

Acids which may be used are in particular acetic acid and propionic acid.

The reaction is carried out either in the absence of a solvent or in an excess of base or acid or in an inert solvent or diluent. For example, alcohols, such as methanol and ethanol, and ethers, such as diethyl ether and methyl tert-butyl ether, are suitable solvents, depending on the reaction conditions.

The reaction can be carried out in general at from 0° C. to the boiling point of the reaction mixture.

Usually, the starting compounds V and VII are used in roughly equimolar amounts, but one of the components may also be used in excess.

Process D:

Reaction of an activated carboxylic acid VIII with a nucleophile IX or of an activated carboxylic acid X with an alcohol HOR$^7$ in a manner known per se (cf. for example J. March, Advanced Organic Chemistry, page 348 et seq.):

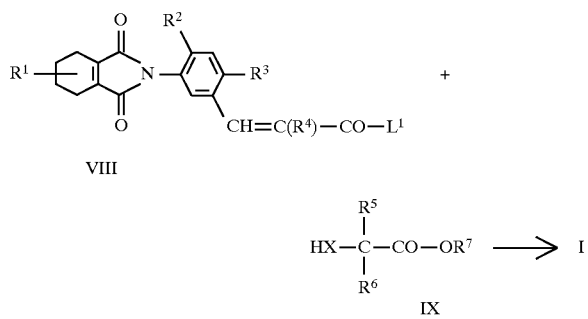

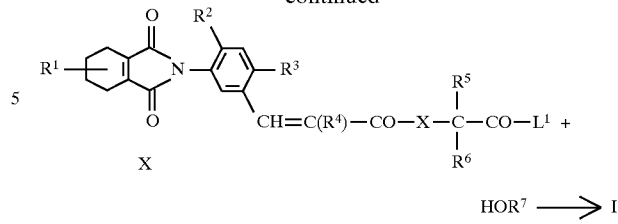

$L^1$ is a conventional leaving group, for example chlorine, bromine or 1-imidazolyl.

If $L^1$ is chlorine or bromine, the presence of a base, such as triethylamine or pyridine, may be advantageous.

Examples of suitable solvents are halohydrocarbons, such as methylene chloride and 1,2-dichloroethane, aromatic hydrocarbons and halohydrocarbons, such as benzene, toluene and chlorobenzene, ethers, such as diethyl ether, tetrahydrofuran, methyl tert-butyl ether and dioxane, dipolar aprotic solvents, such as dimethyl sulfoxide and dimethylformamide, and mixtures of such solvents.

The reaction is carried out in general at from −20° C. to the boiling point of the reaction mixture.

Usually, the starting compounds are used in roughly stoichiometric amounts, unless it is preferable to use one of the components in excess.

The activated carboxylic acids VIII and X where $L^1$ is chlorine or bromine are in turn obtainable in a manner known per se by reacting the corresponding carboxylic acids XI or I where $R^7$ is hydrogen with a halogenating agent, for example with thionyl chloride, thionyl bromide, sulfuryl chloride, sulfuryl bromide, an organic sulfonyl choride, such as tosyl chloride, phosphorus trichloride, phosphorus tribromide, phosphorus pentachloride, phosphorus pentabromide or phosphoryl bromide, or with a binary halogenating system, such as tetrachloromethane/ triphenylphosphine or tetrabromomethane/ triphenylphosphine:

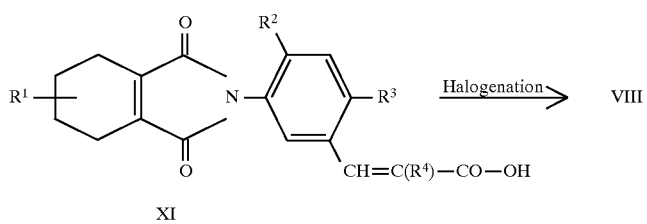

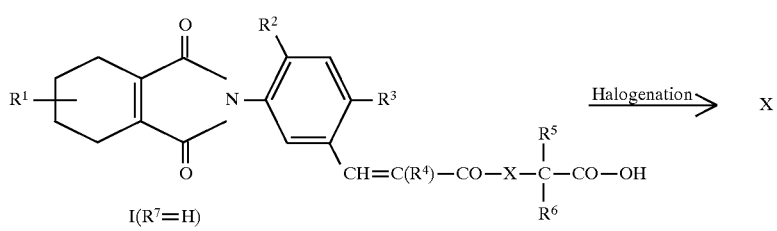

The halogenation can be carried out without a solvent or in an inert solvent. In general, suitable solvents are, for example, halohydrocarbons, such as methylene chloride, chloroform and 1,2-dichloroethane, aromatic hydrocarbons and halohydrocarbons, such as benzene, toluene and chlorobenzene, dipolar aprotic solvents, such as acetonitrile, and carbon disulfide and ethers, such as diethyl ether, methyl tert-butyl ether and tetrahydrofuran, depending on the halogenating agent. Mixtures of these solvents are also suitable.

The halogenation can be carried out at from −30° C. to the boiling point of the reaction mixture.

Depending on the halogenating agent, the acid to be halogenated is advantageously used in a stoichiometric amount or in excess.

In a variant of the process, the activated carboxylic acid VIII or X is prepared in situ, particularly when $L^1$ is 1-imidazolyl or when Mitsunobu conditions are used (O. Mitsunobu, Synthesis 1981, 1).

Process E:

Reaction of an acid derivative XII with an alkylating agent XIII or of a compound I where $R^7$ is hydrogen with an alkylating agent $L^2R^7$ in a manner known per se:

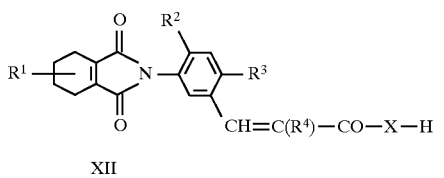

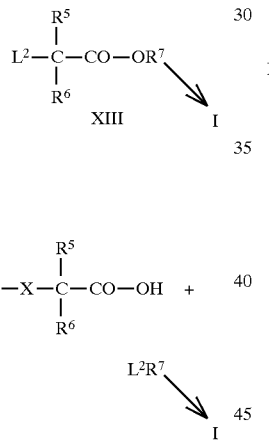

$L^2$ is a conventional leaving group, such as halogen, preferably chlorine, bromine or iodine, alkyl- or haloalkylsulfonyloxy, preferably methylsulfonyloxy or trifluoromethylsulfonyloxy, arylsulfonyloxy, preferably toluenesulfonyloxy, or alkoxysulfonyloxy, preferably methoxysulfonyloxy or ethoxysulfonyloxy.

The reaction is advantageously carried out in an inert solvent, for example in an ether, such as diethyl ether, methyl tert-butyl ether, dimethoxyethane, diethylene glycol dimethyl ether, tetrahydrofuran or dioxane, a ketone, such as acetone, diethyl ketone, ethyl methyl ketone or cyclohexanone, a dipolar aprotic solvent, such as acetonitrile, dimethylformamide, N-methylpyrrolidone or dimethyl sulfoxide, a protic solvent, such as methanol or ethanol, an aromatic hydrocarbon or halohydrocarbon, such as benzene, chlorobenzene or 1,2-dichlorobenzene, a heteroaromatic solvent, such as pyridine or quinoline, or a mixture of such solvents.

Tetrahydrofuran, acetone, diethyl ketone and dimethylformamide are particularly suitable.

The alkylations are usually carried out in the presence of a base, for example the hydroxides, hydrides, alkoxides, carbonates or bicarbonates of alkali metal and alkaline earth metal cations, or tertiary aliphatic amines, such as triethylamine, N-methylmorpholine and N-ethyl-N,N-diisopropylamine, and bicyclic and tricyclic amines, such as diazabicycloundecane (DBU) and diazabicyclooctane (DABCO), and aromatic nitrogen bases, such as pyridine, 4-dimethylaminopyridine and quinoline, being suitable. Combinations of different bases are also possible. Preferred bases are sodium hydride, sodium hydroxide, sodium carbonate, potassium carbonate, sodium methylate, sodium ethylate and potassium tert-butylate.

Usually, the starting materials are used in roughly stoichiometric amounts, but an excess of one or other component may also be advantageous with regard to carrying out the process or for ensuring as complete conversion as possible of XII or of I where $R^7$ is hydrogen.

The molar ratio of acid derivative XII, or I where $R^7$ is hydrogen, to base is in general from 1:1 to 1:3.

The concentration of the starting materials in the solvent is usually from about 0.1 to 5.0 mol/l.

The reaction can be carried out at from 0° C. to the boiling point of the particular reaction mixture.

Process F:

Reaction of a tetrahydrophthalic anhydride XIV with an aminocinnamic acid derivative IIa in a manner known per se:

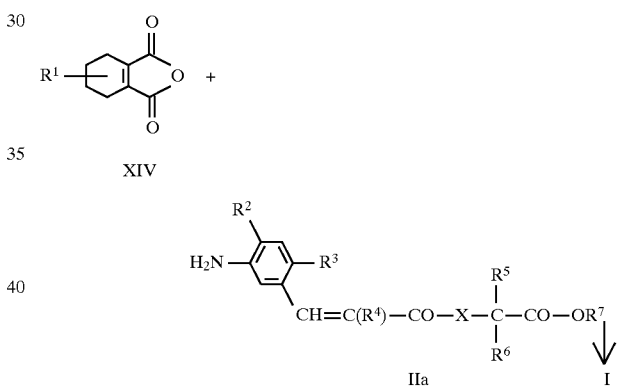

Examples of suitable solvents/diluents are alkanecarboxylic acids, such as acetic acid, propionic acid and isobutyric acid, alkanecarboxylic esters, such as ethyl acetate, aprotic solvents, such as dimethylformamide, dimethyl sulfoxide and N-methylpyrrolidone, and aromatics, such as toluene and the xylenes. When an aprotic solvent is used, it is preferable continuously to remove the water of reaction formed or to carry out acid catalysis (with, for example, p-toluenesulfonic acid, trifluoromethanesulfonic acid, etc.).

The reaction temperature is usually from 0° C. to the boiling point of the reaction mixture.

As a rule, the starting materials are used in roughly stoichiometric amounts, but one or other component may also advantageously be used in an amount of up to about 10 mol % less than or greater than the stoichiometric amount.

The aminocinnamic acid derivatives IIa are novel and in turn are obtainable, for example, by one of the methods described under processes A to E or in a manner known per se (cf. for example Houben-Weyl, Methoden der organischen Chemie, Vol. XI/1, 4th Edition 1957, page 431 et seq.) by reduction of the corresponding nitrocinnamic acid derivatives IIb:

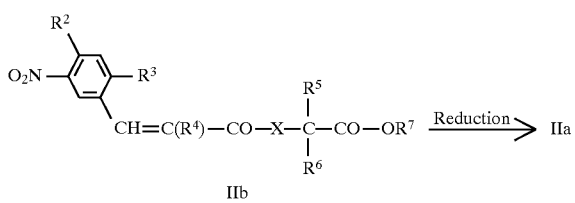

IIb

Particularly suitable reducing agents are
elemental metals, such as iron, tin and zinc,
hydrogen in the presence of suitable catalysts, such as palladium or platinum on carbon or Raney nickel, or
complex hydrides, such as LiAlH$_4$ and NaBH$_4$, in the presence or absence of catalysts.

Suitable solvents are usually carboxylic acids, such as acetic acid and propionic acid, alcohols, such as methanol and ethanol, ethers, such as diethyl ether, methyl tert-butyl ether, tetrahydrofuran and dioxane, aromatics, such as benzene and toluene, and mixtures of said solvents, depending on the reducing agent.

The reactions can be carried out at from −100° C. to the boiling point of the particular reaction mixture.

Usually, the starting compounds are used in roughly stoichiometric amounts; in individual cases, however, an excess of up to about 10 mol % of one or other component may also be advantageous.

The nitrocinnamic acid derivatives IIb are likewise novel and can be prepared, for example, by the methods described under processes A to E.

Unless stated otherwise, all processes described above are advantageously carried out at atmospheric pressure or under the autogenous pressure of the particular reaction mixture.

Starting compounds stated for the individual processes are either known or are obtainable in a manner known per se, for example also by one of the processes described.

The substituted phthalimidocinnamic acid derivatives of the formula I may contain one or more centers of chirality and are then usually obtained as enantiomer or diastereomer mixtures. The mixtures can, if desired, be resolved into the substantially pure isomers by the conventional methods, for example by means of crystallization or chromatography over an optically active adsorbate. Pure optically active isomers can also be prepared, for example, from corresponding optically active starting materials.

The compounds I and their agriculturally useful salts are suitable, both in the form of isomer mixtures and in the form of the pure isomers, as herbicides. The agents containing I are capable of very good control of weeds and grass weeds in crops such as wheat, rice, corn, soybean and cotton, without significantly damaging the crops. This effect occurs in particular at low application rates.

Depending on the particular application method, the compounds I or herbicides containing them may also be used in a further number of crops for eliminating undesirable plants. For example, the following crops are suitable:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N.rustica*), *Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* und *Zea mays*.

Moreover, the compounds I can also be used in crops which are resistant to the action of herbicides as a result of breeding including genetic engineering methods.

The substituted phthalimidocinnamic acid derivatives I are also suitable for the desiccation and/or defoliation of plants.

As desiccants, they are particularly suitable for drying out the above-ground parts of crops, such as potato, rape, sunflower and soybean. This permits completely mechanical harvesting of these important crops.

Facilitating harvesting is also of economic interest and is permitted by the concentrated dropping or reduction of the adhesion to the tree in the case of citrus fruits, olives or other species and varieties of pomes, drupes and indehiscent fruit. The same mechanism, ie. promotion of the formation of abscission tissue between fruit or leaf and shoot part of the plant is also essential for readily controllable defoliation of crops, in particular cotton.

Furthermore, the reduction of the time interval in which the individual cotton plants ripen leads to higher fiber quality after harvesting.

The compounds I and the herbicides containing them can be applied, for example, in the form of directly sprayable aqueous solutions, powders, suspensions, including concentrated aqueous, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure a very fine distribution of the novel active ingredients.

Suitable inert assistants for the preparation of directly sprayable solutions, emulsions, pastes or oil dispersions are essentially mineral oil fractions having a medium to high boiling point, such as kerosene and diesel oil, and coaltar oils and oils of vegetable and animal origin, aliphatic, cyclic and aromatic hydrocarbons, for example paraffins, tetrahydronaphthalene, alkylated naphthalenes and derivatives thereof, alkylated benzenes and derivatives thereof, alcohols, such as methanol, ethanol, propanol, butanol and cyclohexanol, ketones, such as cyclohexanone, strongly polar solvents, for example amines, such as N-methylpyrrolidone, and water.

Aqueous application forms can be prepared from emulsion concentrates, suspensions, pastes, wettable powders or water-dispersible granules by adding water. For the preparation of emulsions, pastes or oil dispersions, the substances, as such or dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvent or oil and which are suitable for dilution with water.

Suitable surfactants are the alkali metal, alkaline earth metal and ammonium salts of aromatic sulfonic acids, for example ligninsulfonic, phenolsulfonic, naphthalenesulfonic and dibutylnaphthalenesulfonic acid, and of fatty acids, alkylsulfonates, alkylarylsulfonates, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of naphthalenesulfonic acids with phenyl and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers, polyoxypropylene alkyl ethers, lauryl alcohol polyglycol ether acetate, sorbitol esters, ligninsulfite waste liquors or methylcellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate or ureas, and vegetable products, such as grain flour, bark meal, wood meal and nutshell meal, cellulosic powders or other solid carriers.

The concentrations of the active ingredients I in the ready-to-use formulations can be varied within wide ranges, for example from 0.01 to 95, preferably from 0.5 to 90, % by weight. The active ingredients are used in a purity of from 90 to 100%, preferably from 95 to 100% (according to the NMR spectrum).

The following formulation examples illustrate the preparation of such formulations:

I. 20 parts by weight of compound No. I0.01 are dissolved in a mixture which consists of 80 parts by weight of alkylated benzene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100 000 parts by weight of water and finely distributing it therein, an aqueous dispersion which contains 0.02% by weight of the active ingredient is obtained.

II. 20 parts by weight of compound No. 1.02 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100 000 parts by weight of water and finely distributing it therein, an aqueous dispersion which contains 0.02% by weight of the active ingredient is obtained.

III. 20 parts by weight of active ingredient No. I0.13 are dissolved in a mixture which consists of 25 parts by weight of cyclohexanone, 65 parts by weight of a mineral oil fraction boiling within the range from 210° to 280° C. and 10 parts by weight of the adduct of 40 mol of ethylene oxide with 1 mol of castor oil. By pouring the solution into 100 000 parts by weight of water and finely distributing it therein, an aqueous dispersion which contains 0.02% by weight of the active ingredient is obtained.

IV. 20 parts by weight of active ingredient No. I0.14 are thoroughly mixed with 3 parts by weight of the sodium salt of diisobutylnaphthalene-$\alpha$-sulfonic acid, 17 parts by weight of the sodium salt of a ligninsulfonic acid from a sulfite waste liquor and 60 parts by weight of silica gel powder, and the mixture is milled in a hammer mill. By finely distributing the mixture in 20 000 parts by weight of water, a spray liquor which contains 0.1% by weight of the active ingredient is obtained.

V. 3 parts by weight of active ingredient No. I0.24 are mixed with 97 parts by weight of finely divided kaolin. A dusting agent which contains 3% by weight of the active ingredient is obtained in this manner.

VI. 20 parts by weight of active ingredient No. I0.15 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The active ingredients I or the herbicides can be applied by the preemergence or postemergence method. If the active ingredients are less well tolerated by certain crops, it is possible to use application methods in which the herbicides are sprayed with the aid of the sprays in such a way that the leaves of the sensitive crops are as far as possible not affected while the active ingredients reach the leaves of undesirable plants growing underneath or the uncovered soil surface (post-directed, lay-by).

The application rates of active ingredient I are from 0.001 to 3.0, preferably from 0.01 to 2, kg/ha of active ingredient (a.i.), depending on the aim of control, the season, the target plants and stage of growth.

In order to broaden the action spectrum and to achieve synergistic effects, the substituted phthalimidocinnamic acid derivatives I can be mixed with a large number of members of other groups of herbicidal or growth-regulating active ingredients and applied together with them. Examples of suitable components of the mixture are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1, 3-dione derivatives which carry, for example, a carboxyl or carbimino group in the 2 position, quinolinecarboxylic acid derivatives, imidazolinones, sulfonamides, sulfonylureas, aryloxy- and hetaryloxyphenoxypropionic acid and their salts, esters and amides and others.

It may also be useful to apply the compounds I, alone or in combination with other herbicides, also as a mixture together with further crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added.

Preparation examples

EXAMPLE 1

N-{4-Chloro-5-[2-(N-ethoxycarbonylmethyl-N-methylaminocarbonyl)-2-chloroethen-1-yl]-2-fluorophenyl}-3,4,5,6-tetrahydrophthalimide (compound No. I0.17)

6 mmol of carbonyldiimidazole were added dropwise to a solution of 5 mmol of N-[4-chloro-5-(2-hydroxycarbonyl-2-chloroethen-1-yl)-2-fluorophenyl]-3,4,5,6- tetrahydrophthalimide in 50 ml of absolute tetrahydrofuran, after which stirring was carried out for one hour at about 20° C. 5 mmol of ethyl sarcosine hydrochloride were then added to the reaction mixture. 5 mmol of triethylamine in 5 ml of tetrahydrofuran were then added dropwise. Stirring was carried out for 48 hours at about 20° C., after which the solvent was removed under reduced pressure from a water-jet pump. The residue was taken up in water, after which the product was extracted with ethyl acetate. The combined organic phases were dried over sodium sulfate and then evaporated down. The crude product was purified by chromatography over silica gel (eluent: 1:2 petroleum ether/ methyl tert-butyl ether). Yield: 0.97 g (40%).

EXAMPLE 2
N-{4-Chloro-3-[2-(1-allyloxycarbonyleth-1-yloxycarbonyl) ethen-1-yl]phenyl}-3,4,5,6-tetrahydrophthalimide (compound No. I0.11)

A solution of 6.5 mmol of 2-allyl 2-bromopropionate in 5 ml of absolute dimethylformamide was added dropwise at 50° C. to a mixture of 5.4 mmol of N-[4-chloro-3-(2-hydroxycarbonylethen-1-yl)phenyl]-3,4,5,6-tetrahydrophthalimide, 5.4 mmol of potassium carbonate and 50 ml of absolute dimethylformamide. Stirring was carried out for 10 hours at 50° C., after which the reaction mixture was cooled. The solvent was then removed under reduced pressure from a water-jet pump. The residue was taken up in water, after which the product was extracted with methyl tert-butyl ether. The combined organic phases were dried over sodium sulfate and then evaporated down. Yield: 2.3 g (96%).

EXAMPLE 3
N-{4-Chloro-5-[2-chloro-2-(1-methoxycarbonyl-1-cyclopropylmethoxycarbonyl)ethen-1-yl]-2-fluorophenyl}-3,4,5,6-tetrahydrophthalimide (compound No. I0.16)

7.9 mmol of triphenylphosphine were added to a solution of 7.2 mmol of N-{4-chloro-5-(2-hydroxycarbonyl-2-chloroethen-1-yl)-2-fluorophenyl}-3,4,5,6-tetrahydrophthalimide and 7.2 mmol of methyl 1-cyclopropyl-1-hydroxyacetate in 30 ml of absolute tetrahydrofuran. 7.9 mmol of diethyl azodicarboxylate in a mixture of 10 ml of tetrahydrofuran and 10 ml of toluene were then added dropwise. Stirring was carried out for 2 hours at about 20° C., after which a further 3.95 mmol of triphenylphosphine and 3.95 mmol of ethyl azodicarboxylate were added to the reaction mixture and stirring was then continued for 12 hours at about 20° C. Thereafter, 1 ml of water was added and, after stirring for a further 10 minutes, three pinches of sodium sulfate were introduced into the reaction mixture. Finally, the undissolved material was filtered off and the filtrate was evaporated down under reduced pressure from a water-jet pump. The crude product was purified by means of chromatography over silica gel (eluent: 2:1 petroleum ether/diethyl ether). Yield: 0.98 g (28%).

Table 8 lists very particularly preferred substituted phthalimidocinnamic acid derivatives of the formula I, which were prepared or can be prepared according to the examples:

TABLE 8

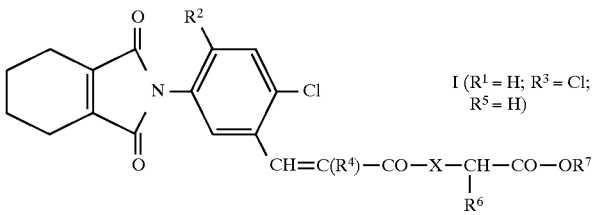

I ($R^1$ = H; $R^3$ = Cl; $R^5$ = H)

| No. | $R^2$ | $R^4$ | X | $R^6$ | $R^7$ | Mp. [°C.] $^1$H-NMR [δ in ppm] |
|---|---|---|---|---|---|---|
| I.01 | H | CH$_3$ | O | CH$_3$ | CH$_2$CH$_3$ | Oil |
| I.02 | H | CH$_3$ | O | C$_2$H$_5$ | CH$_2$CH$_3$ | Oil |
| I.03 | H | Cl | O | CH$_3$ | CH$_3$ | 149–151 |
| I.04 | H | Cl | O | H | CH$_3$ | 113–114 |
| I.05 | H | Cl | O | H | CH$_2$CH$_3$ | 95 |
| I.06 | H | Cl | O | H | C(CH$_3$)$_3$ | 120–121 |
| I.07 | H | Cl | O | C$_2$H$_5$ | C$_2$H$_5$ | 1.00(t, 3H); 1.23(t, 3H); 1.74(m, 4H); 1.93(m, 2H); 2.33(m, 4H); 4.19(q, 2H); 5.12(t, 1H); 7.50(dd, 1H); 7.74(d, 1H); 7.95(d, 1H); 8.18(s, 1H) |
| I.08 | H | H | O | C$_2$H$_5$ | C$_2$H$_5$ | 86 |
| I.09 | H | Br | O | CH$_3$ | CH$_3$ | 1.52(d, 3H); 1.72(brs, 4H); 2.33(brs, 4H); 3.72(s, 3H); 5.26(q, 1H); 7.49(dd, 1H); 7.71(d, 1H); 7.86(d, 1H); 8.37(s, 1H) |
| I.10 | H | Br | O | C$_2$H$_5$ | C$_2$H$_5$ | 1.02(t, 3H); 1.24(t, 3H); 1.71(brs, 4H); 1.92(m, 2H); 2.33(brs, 4H); 4.19(m, 2H); 5.12(t, 1H); 7.50(dd, 1H); 7.72(d, 1H); 7.87(d, 1H); 8.38(s, 1H) |

TABLE 8-continued

I ($R^1$ = H; $R^3$ = Cl; $R^5$ = H)

CH=C($R^4$)—CO—X—CH($R^6$)—CO—O$R^7$

| No. | $R^2$ | $R^4$ | X | $R^6$ | $R^7$ | Mp. [°C.]<br>$^1$H-NMR [δ in ppm] |
|---|---|---|---|---|---|---|
| I.11 | H | H | O | CH$_3$ | CH$_2$CH=CH$_2$ | 1.54(d, 3H); 1.74(brs, 4H); 2.34(brs, 4H); 4.65(d, 2H); 5.22(m, 2H); 5.32(d, 1H); 5.92(m, 1H); 7.23(d, 1H); 7.44(dd, 1H); 7.66(d, 1H); 7.94(d, 1H); 8.00(d, 1H) |
| I.12 | H | H | O | OC$_2$H$_5$ | C$_2$H$_5$ | 114 |
| I.13 | F | Cl | O | CH$_3$ | C$_2$H$_5$ | 1.36(t, 3H); 1.62(d, 3H); 1.82(brs, 4H); 2.47(brs, 4H); 4.27(q, 2H); 5.26(q, 1H); 7.38(d, 1H); 7.98(d, 1H); 8.17(s, 1H); |
| I.14 | F | Cl | O | H | CH$_3$ | 90–91 |
| I.15 | F | Cl | O | CH$_3$ | CH(CH$_3$)$_2$ | 1.28(d, 3H); 1.30(d, 3H); 1.61(d, 3H); 1.84(brs, 4H); 2.46(brs, 4H); 5.08(sept, 1H); 5.20(q, 1H); 7.36(d, 1H); 7.98(d, 1H); 8.16(s, 1H); |
| I.16 | F | Cl | O | cyclopropyl | CH$_3$ | 96–98 |
| I.17 | F | Cl | N(CH$_3$) | H | C$_2$H$_5$ | 1.23(t, 3H); 1.74(brs, 4H); 2.47(brs, 4H); 3.17, 3,34(s, 3H); 4.17(q, 2H); 4.18, 4.36(brs, 2H); 7.00, 7.12(s, 1H); 7.34(m, 2H); |
| I.18 | F | Cl | NH | H | C$_2$H$_5$ | 132–133 |
| I.19 | F | Cl | NH | CH$_2$-phenyl | CH$_2$CH$_3$ | 1.26(t, 3H); 1.86(brs, 4H); 2.44(brs, 4H); 3.24(d, 2H); 4.20(q, 2H); 4.92(q, 1H); 7.16(d, 2H); 7.26(m, 5H); 7.80(d, 1H); 8.16(s, 1H); |
| I.20 | F | Cl | NH | CH$_2$CH(CH$_3$)$_2$ | CH$_3$ | 0.99(d, 6H); 1.72(m, 3H); 1.84(brs, 4H); 2.46(brs, 4H); 3.78(s, 3H); 4.74(dt, 1H); 7.18(d, 1H); 7.36(d, 1H); 7.79(d, 1H); 8.16(s, 1H); |
| I.21 | F | Cl | NH | CH(CH$_3$)$_2$ | CH$_3$ | 1.00(dd, 6H); 1.82(brs, 4H); 2.45(brs, 4H); 2.48(m, 1H); 3.80(s, 3H); 4.63(dd, 1H); 7.28(d, 1H); 7.38(d, 1H); 7.83(d, 1H); 8.15(s, 1H); |
| I.22 | F | Cl | NH | CH$_3$ | CH$_2$CH$_3$ | 1.30(brs, 3H); 1.55(brs, 3H); 1.83(brs, 4H); 2.46(brs, 4H); 4.24(brs, 2H); 4.65(brs, 1H); 7.38(d, 1H); 7.55(d, 1H); 7.82(d, 1H); 8.16(s, 1H); |
| I.23 | F | Cl | NH | CH$_3$ | CH$_3$ | 1.58(d, 3H); 1.84(brs, 4H); 2.43(brs, 4H); 3.82(s, 3H); 4.86(q, 1H); 7.36(d, 1H); 7.80(d, 1H); 8.18(s, 1H); 9.36(brs, 1H) |
| I.24 | H | CH$_3$ | O | H | CH$_3$ | 80–81 |
| I.25 | F | Cl | N(CH$_3$) | H | CH$_3$ | 1.82(brs, 4H); 2.44(brs, 4H); 3.10–3.22(brs, 3H); 3.75(s, 3H); 4.22(brs, 2H); 7.06(d, 1H); 7.38(d, 1H); 7.80(brs, 1H) |

Use examples (herbicidal activity)

The herbicidal activity of the substituted phthalimidocinnamic acid derivatives I was demonstrated by the following greenhouse experiments:

The culture vessels used were plastic flowerpots containing loamy sand with about 3.0% of humus as substrate. The seeds of the test plants were sown separately according to species.

In the preemergence treatment, the active ingredients suspended or emulsified in water were applied directly after sowing, by means of finely distributing nozzles. The vessels were lightly sprinkle-irrigated in order to promote germination and growth and were then covered with transparent plastic covers until the plants had begun to grow. This covering ensures uniform germination of the test plants, unless this has been adversely affected by the active ingredients.

For the postemergence treatment, the test plants were first grown to a height of growth of from 3 to 15 cm, depending on the form of growth, before being treated with the active ingredients suspended or emulsified in water. For this purpose, the test plants were either directly sown and grown in the same vessels or were first grown separately as seedlings and transplanted into the test vessels a few days before the treatment. The application rate for the postemergence treatment was 0.0625, 0.0313, 0.0156 or 0.0078 kg/ha of a.i.

The plants were kept at 10°–25° C. or 20°–35° C., according to species. The test period extended over 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal course of growth.

The plants used in the greenhouse experiments consisted of the following species:

| Botanical name | Common name |
| --- | --- |
| Amaranthus retroflexus | carelessweed; redroot pigweed; common amaranth |
| Chenopodium album | lambsquarters; pigweed; fat-hen; white goosefoot |
| Chrysanthemum coronarium | crown daisy; garland chrysanthumum |
| Galium aparine | catchweed bedstraw |
| Ipomoea subspecies | morningglory |
| Matricaria inodora | false chamomille; scentless chamomille; false mayweed; |
| Polygonum persicaria | lady's thumb; redshank |
| Sida spinosa | prickly sida; teaweed |
| Solanum nigrum | black nightshade |
| Triticum aestivum | winter wheat |

At an application rate of 0.0625 or 0.0313 kg/ha of a.i., compound No. I0.24 had a very good action against Galium aparine and Solanum nigrum in wheat.

At an application rate of 0.0156 or 0.0078 kg/ha of a.i. in the postemergence method, compound no. I0.01 controlled Chenopodium album, Chrysanthemum coronarium, Ipomoea subspecies and Polygonum persicaria better than the comparative compound A disclosed in EP-A 240659.

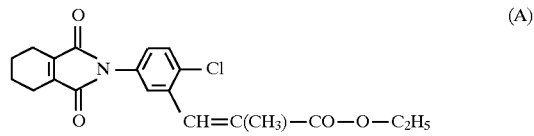

At an application rate of 0.625 or 0.0313 kg/ha of a.i. in the postemergence method, compound no. 1.08 was more effective in the test on Amaranthus retroflexus, Chenopodium album, Ipomoea subspecies, Matricaria inodora and Sida spinosa than the comparative compounds B and C disclosed in EP-A 240659.

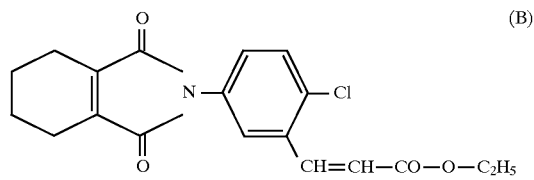

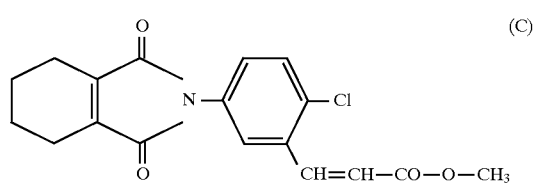

Use examples (desiccant/defoliant activity)

The test plants used were young, 4-leaf cotton plants (without cotyledons), which were grown under greenhouse conditions (relative humidity from 50 to 70%; day/night temperature 27°/20° C.).

The foliage of the young cotton plants was treated to run-off with aqueous formulations of the active ingredients (with the addition of 0.15% by weight, based on the spray liquor, of the fatty alcohol alkoxylate Plurafac LF 700). The amount of water applied was equivalent to 1000 l/ha. After 13 days, the number of dropped leaves and the degree of defoliation in % were determined.

No dropping of leaves occurred in the case of the untreated control plants.

We claim:

1. A substituted phthalimidocinnamic acid derivative of the formula I

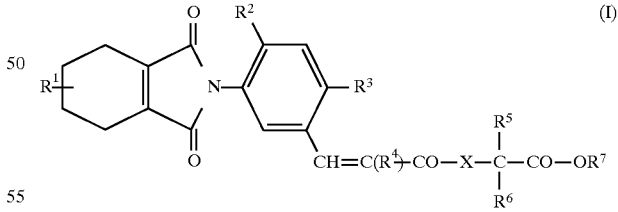

where
 $R^1$ is hydrogen or $C_1$–$C_4$-alkyl;
 $R^2$ is hydrogen or halogen;
 $R^3$ is cyano, nitro, halogen, $C_1$–$C_6$-alkyl, $C_1$–$C_6$-haloalkyl, $C_1$–$C_6$-alkoxy or $C_1$–$C_6$-haloalkoxy;
 $R^4$ is hydrogen, cyano, nitro, halogen or $C_1$–$C_6$-alkyl;
 $R^5$ is hydrogen, $C_1$–$C_6$-alkyl, $C_2$–$C_6$-alkenyl, $C_2$–$C_6$-alkynyl, $C_1$–$C_6$-haloalkyl, $C_1$–$C_6$-cyanoalkyl, $C_1$–$C_6$-hydroxyalkyl, $C_1$–$C_6$-mercaptoalkyl, $C_1$–$C_6$-alkoxy-$C_1$–$C_6$-alkyl or $C_1$–$C_6$-alkylthio-$C_1$–$C_6$-alkyl;

$R^6$ is one of the radicals stated under $R^5$ or cyano, nitro, $C_1$–$C_6$-alkoxy, $C_1$–$C_6$-haloalkoxy, $C_1$–$C_6$-alkylthio, $C_1$–$C_6$-haloalkylthio, $C_3$–$C_6$-cycloalkyl, $C_3$–$C_6$-cycloalkyl-$C_1$–$C_6$-alkyl, ($C_1$–$C_6$-alkoxy) carbonyl-$C_1$–$C_6$-alkyl, hydroxycarbonyl-$C_1$–$C_6$-alkyl, ($C_1$–$C_6$-alkyl amino) carbonyl-$C_1$–$C_6$-alkyl, di($C_1$–$C_6$-alkyl) aminocarbonyl-$C_1$–$C_6$-alkyl, aminocarbonyl-$C_1$–$C_6$-alkyl, ($C_1$–$C_6$-alkyl )carbonyl-$C_1$–$C_6$-alkyl, $C_1$–$C_6$-alkoximino-$C_1$–$C_6$-alkyl, hydroximino-$C_1$–$C_6$-alkyl, di ($C_1$–$C_6$-alkoxy)-$C_1$–$C_6$-alkyl, di ($C_1$–$C_6$-alkylthio) - $C_1$–$C_6$-alkyl, $C_3$–$C_6$-haloalkenyl, ($C_1$–$C_6$-alkoxy) carbonyl, hydroxycarbonyl, ($C_1$–$C_6$-alkylamino) carbonyl, di($C_1$–$C_6$-alkyl )aminocarbonyl, aminocarbonyl ($C_1$–$C_6$-alkyl) carbonyl, ($C_1$–$C_6$-haloalkyl) carbonyl, aryl, hetaryl, aryl-$C_1$–$C_6$-alkyl or hetaryl-$C_1$–$C_6$-alkyl, where the aryl and hetaryl rings may, optionally, carry from one to three radicals selected from the group consisting of cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, hydroxyl, mercapto and ($C_{1-6}$-alkoxy)carbonyl;

or $R^5$ and $R^6$ together form a two-membered to six-membered alkylene chain in which a methylene unit may be replaced by oxygen or $C_1$–$C_4$-alkylimino;

$R^7$ is hydrogen, $C_1$–$C_6$-alkyl, $C_3$–$C_6$-alkenyl, $C_3$–$C_6$-alkynyl, $C_2$–$C_6$-haloalkyl, $C_1$–$C_6$-cyanoalkyl, $C_1$–$C_6$-alkoxy-$C_2$–$C_6$-alkyl, $C_1$–$C_6$-alkylthio-$C_2$–$C_6$-alkyl, ($C_1$–$C_6$-alkoxy)carbonyl-$C_1$–$C_6$-alkyl, $C_3$–$C_6$-cycloalkyl, $C_3$–$C_6$-cycloalkyl-$C_1$–$C_6$-alkyl, phenyl or benzyl, where the phenyl rings may each carry from one to three radicals selected from the group consisting of cyano, nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio and ($C_1$–$C_6$-alkoxy)carbonyl;

X —$N(R^8)$—, and $R^8$ is one of the radicals stated under $R^7$ or is ($C_1$–$C_6$-alkoxy)carbonyl, ($C_1$–$C_6$-haloalkoxy)carbonyl, ($C_1$–$C_6$-alkyl)carbonyl, ($C_1$–$C_6$-haloalkyl)carbonyl, tri ($C_1$–$C_6$-alkyl)silyl, aryloxycarbonyl or arylmethoxycarbonyl or, together with $R^6$, is a three-membered to 5-membered alkylene chain in which a nonterminal methylene unit may be replaced by oxygen or $C_1$–$C_4$-alkylimino or in which the N-bonded methylene unit may be replaced by carbonyl, and the agriculturally useful salts of I.

2. A substituted phthalimidocinnamic acid derivative of the formula I as claimed in claim 1, where $R^3$ is halogen or cyano and X is —$N(R^8)$—.

3. A substituted phthalimidocinnamic acid derivative of the formula I as claimed in claim 1, where $R^2$ is hydrogen, fluorine or chlorine.

4. An amino- or nitrocinnamic acid derivative of the formula IIa or IIb

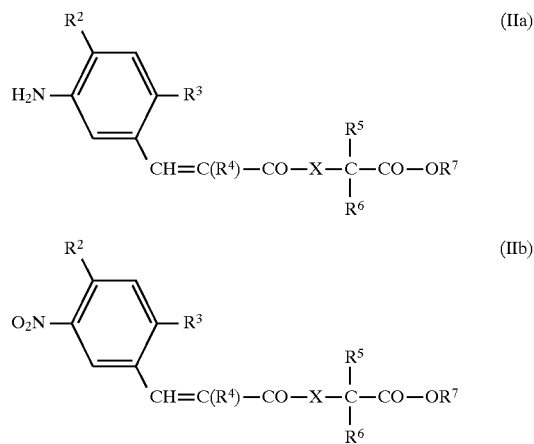

where $R^2$ to $R^7$ and X have the meanings stated in claim 1.

5. A herbicide containing a herbicidal amount of at least one substituted phthalimidocinnamic acid derivative of the formula I or an agriculturally useful salt of I, as defined in claim 1, and at least one inert liquid or solid carrier and, optionally at least one surfactant.

6. A plant desiccant or defoliant containing an amount, effective for desiccation or defoliation, of at least one substituted phthalimidocinnamic acid derivative of the formula I or an agriculturally useful salt of I, as defined in claim 1, and at least one inert liquid or solid carrier and, optionally, at least one surfactant.

7. A process for the preparation of a herbicide, wherein a herbicidal amount of at least one substituted phthalimidocinnamic acid derivative of the formula I or an agriculturally useful salt of I, as defined in claim 1, and at least one inert liquid or solid carrier and, optionally, at least one surfactant are mixed.

8. A process for the preparation of a desiccant or defoliant, wherein an amount, effective for desiccation or defoliation, of at least one substituted phthalimidocinnamic acid derivative of the formula I or an agriculturally useful salt of I, as defined in claim 1, and at least one inert liquid or solid carrier and, optionally, at least one surfactant are mixed.

9. A method for controlling undesirable plant growth, wherein a herbicidal amount of at least one substituted phthalimidocinnamic acid derivative of the formula I or one agriculturally useful salt of I, as defined in claim 1, is allowed to act on plants or their habitat or on seed.

10. A method for the desiccation or defoliation of plants, wherein an amount, effective for desiccation or defoliation, of at least one substituted phthalimidocinnamic acid derivative of the formula I or one agriculturally useful salt of I, as defined in claim 1, is allowed to act on plants.

11. A process for the preparation of a substituted phthalimidocinnamic acid derivative of the formula I as defined in claim 1, where $R^4$ is chlorine or bromine, wherein an aniline of the formula III

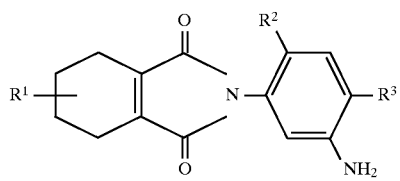

and a propynoic acid derivative IV

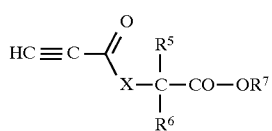

are subjected to a Meerwein alkylation reaction.

12. A process for the preparation of a substituted phthalimidocinnamic acid derivative of the formula I as defined in claim 1, wherein a benzaldehyde of the formula V

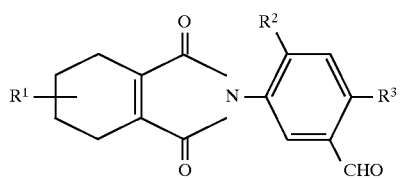

is reacted with an ylide of the formula VI

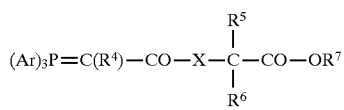

where Ar is an aromatic radical which, optionally, may be substituted.

13. A process for the preparation of a substituted phthalimidocinnamic acid derivative of the formula I as defined in claim 1, where $R^4$ is nitro or cyano, wherein a benzaldehyde of the formula V

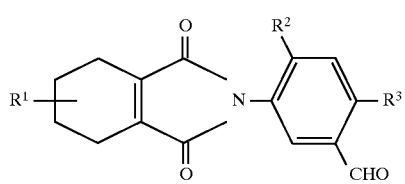

is reacted with a CH-acidic compound of the formula VII:

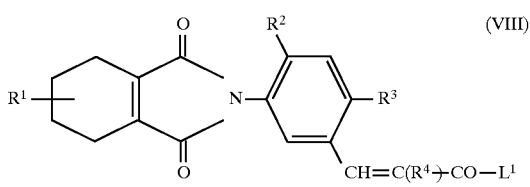

14. A process for the preparation of a substituted phthalimidocinnamic acid derivative of the formula I as defined in claim 1, wherein either an activated carboxylic acid of the formula VIII

where $L^1$ is a conventional leaving group, is reacted with a nucleophile of the formula IX $$HX-\overset{R^5}{\underset{R^6}{C}}-CO-OR^7 \quad (IX)$$

or an activated carboxylic acid of the formula X

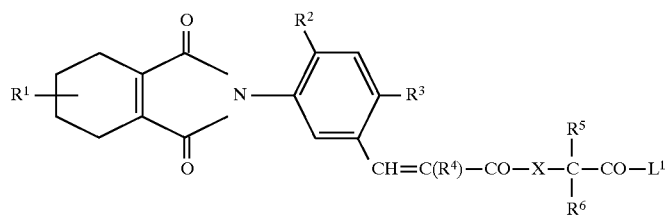

is reacted with an alkohol $HOR^7$.

15. A process for the preparation of a substituted phthalimidocinnamic acid derivative of the formula I as defined in claim 1, wherein either an acid derivative XII

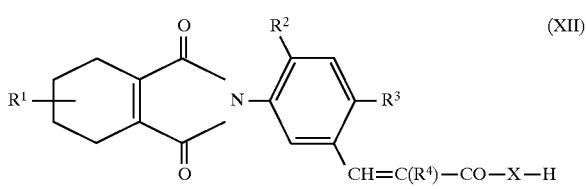

is reacted with an alkylating agent XIII

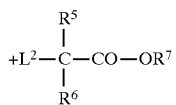 (XIII)

where $L^2$ is a conventional leaving group,
or a compound I as claimed in claim 1, where $R^7$ is hydrogen, is reacted with an alkylating agent $L^2R^7$.

16. A process for the preparation of a substituted phthalimidocinnamic acid derivative of the formula I as defined in claim 1, wherein a tetrahydrophthalic anhydride of the formula XIV

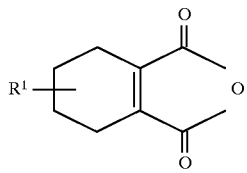 (XIV)

is reacted with an aminocinnamic acid derivative IIa

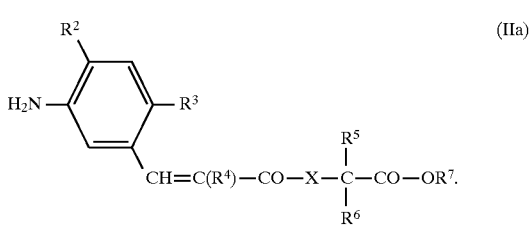 (IIa)

17. A process for the preparation of a nitrocinnamic acid derivative of the formula IIb as defined in claim 4, wherein a correspondingly substituted aminocinnamic acid derivative IIa is reduced.

* * * * *

UNITED STATES PATENT AND TRADEMARK OFFICE
CERTIFICATE OF CORRECTION

PATENT NO.: 5,807,807

DATED: September 15, 1998

INVENTOR(S): HEISTRACHER et al.

It is certified that error appears in the above-identified patent and that said Letters Patent is hereby corrected as shown below:

Col. 51, claim 1, line 7, "alkyl$_1$" should be --alkyl,--.

Col. 51, claim 1, line 25, "$C_1$-$_6$" should be -- $C_1$-$C_6$- --.

Col. 51, claim 1, line 44, after "X", insert --is--.

Col. 52, claim 5, line 26, after "optionally" insert --,--.

Signed and Sealed this

Twenty-second Day of December, 1998

Attest:

BRUCE LEHMAN

Attesting Officer

Commissioner of Patents and Trademarks